(12) United States Patent
Fennimore et al.

(10) Patent No.: US 8,465,849 B2
(45) Date of Patent: Jun. 18, 2013

(54) DEUTERATED ZIRCONIUM COMPOUND FOR ELECTRONIC APPLICATIONS

(75) Inventors: Adam Fennimore, Wilmington, DE (US); Weiying Gao, Landenberg, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 364 days.

(21) Appl. No.: 12/643,576

(22) Filed: Dec. 21, 2009

(65) Prior Publication Data

US 2011/0148287 A1    Jun. 23, 2011

(51) Int. Cl.
*H01L 51/54* (2006.01)

(52) U.S. Cl.
USPC ........ 428/690; 428/917; 257/40; 257/E51.05; 313/504; 313/505; 313/506; 546/7; 546/18

(58) Field of Classification Search
USPC ....... 428/690, 917; 257/40, E51.05; 313/504, 313/505, 506; 546/7, 18
See application file for complete search history.

(56) References Cited

U.S. PATENT DOCUMENTS

| | | | |
|---|---|---|---|
| 3,849,458 A | 11/1974 | Dinh | |
| 5,247,190 A | 9/1993 | Friend et al. | |
| 5,408,109 A | 4/1995 | Heeger et al. | |
| 6,677,060 B2 | 1/2004 | Li et al. | |
| 6,875,524 B2 | 4/2005 | Hatwar et al. | |
| 6,902,833 B2 | 6/2005 | Thompson et al. | |
| 2003/0134140 A1* | 7/2003 | Li et al. | 428/621 |
| 2004/0102577 A1 | 5/2004 | Hsu et al. | |
| 2004/0127637 A1 | 7/2004 | Hsu et al. | |
| 2005/0063638 A1 | 3/2005 | Alger et al. | |
| 2005/0158577 A1 | 7/2005 | Ishibashi et al. | |
| 2005/0184287 A1 | 8/2005 | Herron et al. | |
| 2005/0205860 A1 | 9/2005 | Hsu et al. | |
| 2007/0292713 A9 | 12/2007 | Dobbs et al. | |
| 2008/0286566 A1* | 11/2008 | Prakash | 428/332 |
| 2008/0286605 A1 | 11/2008 | Takeda | |
| 2009/0295274 A1 | 12/2009 | Hwang et al. | |
| 2010/0270916 A1 | 10/2010 | Xia et al. | |

FOREIGN PATENT DOCUMENTS

| | | |
|---|---|---|
| EP | 443861 B1 | 7/1995 |
| WO | 2004-058913 | 7/2004 |
| WO | 2005052027 A1 | 6/2005 |
| WO | 2006095951 A1 | 9/2006 |
| WO | 2007021117 A1 | 2/2007 |
| WO | 2008-078114 | 7/2008 |
| WO | 2010-075421 | 7/2010 |

OTHER PUBLICATIONS

International Search Report, PCTUS2010/061677, dated Sep. 27, 2011.
Boix et al., "Efficient H-D Exchange of Aromatic Compounds in Near-Critical D20 Catalysed by a Polymer-Supported Sulphonic Acid," Tetrahedron Letters 40, 1999, pp. 4433-4436.

(Continued)

*Primary Examiner* — Jennifer Chriss
*Assistant Examiner* — Gregory Clark

(57) ABSTRACT

This invention relates to deuterated electron transfer compounds useful in electronic applications. It also relates to electronic devices in which the electron transfer layer includes zirconium compounds with at least one of the aryl compounds containing some deuteration.

2 Claims, 1 Drawing Sheet

OTHER PUBLICATIONS

Esaki et al., "Efficient H/D Exchange Reactions of Alkyl-Substituted Benzene Derivatives by Means of the Pd/C—H2—D2O System," Chemistry—A European Journal, 2007, vol. 13, pp. 4052-4063.

Guo et al., "Aromatic H/D Exchange Reaction Catalyzed by Groups 5 and 6 Metal Chlorides," Chinese Journal of Chemistry, 2005, vol. 23, pp. 341-344.

Gustafsson et al., "Flexible Light-Emitting Diodes Made from Soluble Conducting Polymers," Nature, 1992, vol. 357, pp. 477-479.

Markus et al., Electronics and Nuleonics Dictionary, pp. 470-471 & 476 (McGraw-Hill 1966).

Nguyen et al., "Isotope Effect in Spin Response of π-conjugated Polymer Films and Devices," Nature Materials, 2010, vol. 9, pp. 345-352.

Perrin et al., "No Contribution of an Inductive Effect to Secondary Deuterium Isotope Effects on Acidity," Angewandte Chemie International Edition, 2011, vol. 50, pp. 7674-7676.

Sajiki et al., "Efficient C—H/C—D Exchange Reaction on the Alkyl Side Chain of Aromatic Compounds Using Heterogeneous Pd/C in D2O," Organic Letters, 2004, vol. 6 (9), pp. 1485-1487.

Wang, "Photoconductive Materials," Kirk-Othmer Encyclopedia of Chemical Technology, Fourth Edition, 1996, vol. 18, pp. 837-860.

Watts et al., "A novel deuterium effect on dual charge-transfer and ligand-field emission of the cis-dichlorobis(2,2'-bipyridine)iridium(III) ion," Journal of the American Chemical Society, 1979, vol. 101(10), pp. 2742-2743.

Tong et al., "Enhancement of OLED Efficiencies and High-Voltage Stabilities of Light-Emitting Materials by Deuteration," Journal of Physical Chemistry, 2007, vol. 111, pp. 3490-3494.

* cited by examiner

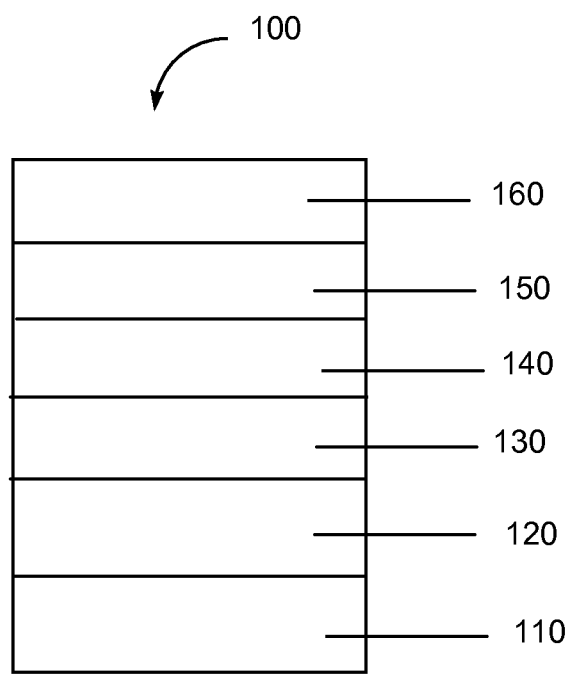

DEUTERATED ZIRCONIUM COMPOUND FOR ELECTRONIC APPLICATIONS

BACKGROUND

1. Field of the Disclosure

This invention relates to zirconium compounds where at least one aryl constituent is at least partially deuterated. It also relates to electronic devices in which at least one electron transfer layer includes such a compound.

2. Description of the Related Art

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules such as anthracene, thiadiazole derivatives, and coumarin derivatives are known to show electroluminescence. Semiconductive conjugated polymers have also been used as electroluminescent components, as has been disclosed in, for example, U.S. Pat. No. 5,247,190, U.S. Pat. No. 5,408,109, and Published European Patent Application 443 861. In many cases the electroluminescent compound is present as a dopant in a host material.

There is a continuing need for new materials for electronic devices.

SUMMARY

There is provided a zirconium compound having aryl constituents, at least one of the aryl constituents having at least one deuterium attached to the aryl constituent.

There is also provided an electronic device comprising an electron transport layer comprising the zirconium compound.

There is further provided at least one deuterium attached to at least one of the aryl constituents in the zirconium compound and, one or more additional layers of the electronic device containing deuterium substitution.

BRIEF DESCRIPTION OF THE DRAWINGS

Embodiments are illustrated in the accompanying figures to improve understanding of concepts as presented herein.

FIG. 1 includes an illustration of one example of an organic electronic device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments are disclosed herein and are exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Deuterated Compound, the Electronic Device, and finally Examples.

1. DEFINITIONS AND CLARIFICATION OF TERMS

Before addressing details of embodiments described below, some terms are defined or clarified.

As used herein, the term "aliphatic ring" is intended to mean a cyclic group that does not have delocalized pi electrons. In some embodiments, the aliphatic ring has no unsaturation. In some embodiments, the ring has one double or triple bond.

The term "alkoxy" refers to the group RO—, where R is an alkyl.

The term "alkyl" is intended to mean a group derived from an aliphatic hydrocarbon having one point of attachment, and includes a linear, a branched, or a cyclic group. The term is intended to include heteroalkyls. The term "hydrocarbon alkyl" refers to an alkyl group having no heteroatoms. The term "deuterated alkyl" is a hydrocarbon alkyl having at least one available H replaced by D. In some embodiments, an alkyl group has from 1-20 carbon atoms.

The term "branched alkyl" refers to an alkyl group having at least one secondary or tertiary carbon. The term "secondary alkyl" refers to a branched alkyl group having a secondary carbon atom. The term "tertiary alkyl" refers to a branched alkyl group having a tertiary carbon atom. In some embodiments, the branched alkyl group is attached via a secondary or tertiary carbon.

The term "aryl" is intended to mean a group derived from an aromatic hydrocarbon having one point of attachment. The term "aromatic compound" is intended to mean an organic compound comprising at least one unsaturated cyclic group having delocalized pi electrons. The term is intended to include heteroaryls. The term "hydrocarbon aryl" is intended to mean aromatic compounds having no heteroatoms in the ring. The term aryl includes groups which have a single ring and those which have multiple rings which can be joined by a single bond or fused together. The term "deuterated aryl" refers to an aryl group having at least one available H bonded directly to the aryl replaced by D. The term "arylene" is intended to mean a group derived from an aromatic hydrocarbon having two points of attachment. In some embodiments, an aryl group has from 3-60 carbon atoms.

The term "aryloxy" refers to the group RO—, where R is an aryl.

The term "compound" is intended to mean an electrically uncharged substance made up of molecules that further consist of atoms, wherein the atoms cannot be separated by physical means. The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond).

The term "deuterated" is intended to mean that at least one H has been replaced by D. The deuterium is present in at least 100 times the natural abundance level. A "deuterated derivative" of compound X has the same structure as compound X, but with at least one D replacing an H.

The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material.

The term "electroactive" when referring to a layer or material, is intended to mean a layer or material that exhibits electronic or electro-radiative properties. In an electronic device, an electroactive material electronically facilitates the operation of the device. Examples of electroactive materials include, but are not limited to, materials which conduct, inject, transport, or block a charge, where the charge can be either an electron or a hole, and materials which emit radiation or exhibit a change in concentration of electron-hole pairs when receiving radiation. Examples of inactive materials include, but are not limited to, planarization materials, insulating materials, and environmental barrier materials.

The prefix "hetero" indicates that one or more carbon atoms have been replaced with a different atom. In some embodiments, the different atom is N, O, or S.

The term "host material" is intended to mean a material to which a dopant is added. The host material may or may not have electronic characteristic(s) or the ability to emit, receive, or filter radiation. In some embodiments, the host material is present in higher concentration.

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating. Discontinuous deposition techniques include, but are not limited to, ink jet printing, gravure printing, and screen printing.

The term "organic electronic device" or sometimes just "electronic device" is intended to mean a device including one or more organic semiconductor layers or materials. All groups can be substituted or unsubstituted unless otherwise indicated. In some embodiments, the substituents are selected from the group consisting of D, halide, alkyl, alkoxy, aryl, aryloxy, cyano, and $NR_2$, where R is alkyl or aryl.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The IUPAC numbering system is used throughout, where the groups from the Periodic Table are numbered from left to right as 1-18 (CRC Handbook of Chemistry and Physics, $81^{st}$ Edition, 2000).

2. DEUTERATED COMPOUND

The deuterated zirconium compound contains aryl constituents having at least one D. In some embodiments, the compound is at least 10% deuterated. By this is meant that at least 10% of the H are replaced by D. In some embodiments, the compound is at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated. In some embodiments, the compounds are 100% deuterated.

In one embodiment, the zirconium compound has the following structure:

1. A zirconium compound comprising:

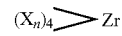

where n=1-4
$X_n =$

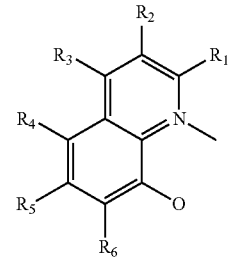

wherein:
R$_1$ through R$_6$ are the same or different at each occurrence and are selected from the group consisting of H, D, alkyl, alkoxy, aryl, aryloxy, siloxane, and silyl; and at least one of R$_1$ through R$_6$ contain at least one D.

In some embodiments, the at least one D is one of R$_1$ through R$_6$ on the aryl ring.

In some embodiments of the compound, at least one of R$_1$ through R$_6$ is D. In some embodiments, at least two of R$_1$ through R$_6$ are D. In some embodiments, at least three are D; in some embodiments, at least four are D; in some embodiments, at least five are D. In some embodiments, all of R$_1$ through R$_6$ are D.

In some embodiments, R$_1$ through R$_6$ are selected from H and D. In some embodiments, one of R$_1$ through R$_6$ is D and five are H. In some embodiments, two of R$_1$ through R$_6$ are D and four are H. In some embodiments, three of R$_1$ through R$_6$ are D and three are H. In some embodiments, four of R$_1$ through R$_6$ are D, and two are H. In some embodiments, five of R$_1$ through R$_6$ are D and one is H. In some embodiments, six of R$_1$ through R$_6$ are D.

In some embodiments, at least one of R$_1$ through R$_6$ is selected from alkyl, alkoxy, aryl, aryloxy, siloxane, and silyl.

In some embodiments of $X_n$ a heteroaryl group contains the deuteration. In some embodiments, the heteroaryl group is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated. In some embodiments, the heteroaryl group is 100% deuterated.

A non-limiting example of a zirconium compound includes the following:

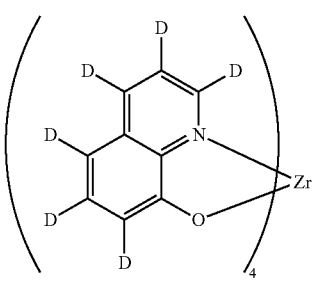

The non-deuterated analog compounds can be made using any technique that will yield a C—C or C—N bond. A variety of such techniques are known, such as Suzuki, Yamamoto, Stille, and Pd- or Ni-catalyzed C—N couplings. The new deuterated compound can then be prepared in a similar manner using deuterated precursor materials or, more generally, by treating the non-deuterated compound with deuterated solvent, such as d6-benzene, in the presence of a Lewis acid H/D exchange catalyst, such as aluminum trichloride or ethyl aluminum chloride, or acids such as $CF_3COOD$, DCl, etc. Exemplary preparations are given in the Examples. The level of deuteration can be determined by NMR analysis and by mass spectrometry, such as Atmospheric Solids Analysis Probe Mass Spectrometry (ASAP-MS). The starting materials of the perdeuterated or partially deuterated aromatic compounds or alky compounds can be purchased from the commercial source or can be obtained using known methods. Some examples of such methods can be found in a) "Efficient H/D Exchange Reactions of Alkyl-Substituted Benzene Derivatives by Means of the Pd/C—H2-D2O System" Hiroyoshi Esaki, Fumiyo Aoki, Miho Umemura, Masatsugu Kato, Tomohiro Maegawa, Yasunari Monguchi, and Hironao Sajiki Chem. Eur. J. 2007, 13, 4052-4063. b) "Aromatic H/D Exchange Reaction Catalyzed by Groups 5 and 6 Metal Chlorides" GUO, Qiao-Xia, SHEN, Bao-Jian; GUO, Hai-Qing TAKAHASHI, Tamotsu *Chinese Journal of Chemistry*, 2005, 23, 341-344; c) "A novel deuterium effect on dual charge-transfer and ligand-field emission of the cis-dichlorobis(2,2'-bipyridine)iridium(III) ion" Richard J. Watts, Shlomo Efrima, and Horia Metiu *J. Am. Chem. Soc.*, 1979, 101 (10), 2742-2743; d) "Efficient H-D Exchange of Aromatic Compounds in Near-Critical D2O Catalysed by a Polymer-Supported Sulphonic Acid" Carmen Boix and Martyn Poliakoff Tetrahedron Letters 40 (1999) 4433-4436; e) U.S. Pat. No. 3,849,458; f) "Efficient C—H/C-D Exchange Reaction on the Alkyl Side Chain of Aromatic Compounds Using Heterogeneous Pd/C in D2O" Hironao Sajiki, Fumiyo Aoki, Hiroyoshi Esaki, Tomohiro Maegawa, and Kosaku Hirota *Org. Lett.*, 2004, 6 (9), 1485-1487.

The compounds described herein can be formed into films using liquid deposition techniques. Surprisingly and unexpectedly, these compounds have greatly improved properties when compared to analogous non-deuterated compounds. Electronic devices including an electron transport layer, also referred to as an electron transfer layer, with the compounds described herein, have improved lifetimes. In addition, the lifetime increases are achieved in combination with high quantum efficiency and good color saturation. Furthermore, the deuterated compounds described herein have greater air tolerance than the non-deuterated analogs. This can result in greater processing tolerance both for the preparation and purification of the materials and in the formation of electronic devices using the materials.

3. ELECTRONIC DEVICE

Organic electronic devices that may benefit from having one or more layers comprising the deuterated zirconium materials described herein include, but are not limited to, (1) devices that convert electrical energy into radiation (e.g., a light-emitting diode, light emitting diode display, or diode laser), (2) devices that detect signals through electronics processes (e.g., photodetectors, photoconductive cells, photoresistors, photoswitches, phototransistors, phototubes, IR detectors), (3) devices that convert radiation into electrical energy, (e.g., a photovoltaic device or solar cell), and (4) devices that include one or more electronic components that include one or more organic semi-conductor layers (e.g., a transistor or diode).

One illustration of an organic electronic device structure is shown in FIG. 1. The device 100 has a first electrical contact layer, an anode layer 110 and a second electrical contact layer, a cathode layer 160, and an electroactive layer 140 between them. Adjacent to the anode may be a hole injection layer 120. Adjacent to the hole injection layer may be a hole transport layer 130, comprising hole transport material. Adjacent to the cathode may be an electron transport layer 150, comprising an electron transport material. Devices may use one or more additional hole injection or hole transport layers (not shown) next to the anode 110 and/or one or more additional electron injection or electron transport layers (not shown) next to the cathode 160.

Layers 120 through 150 are individually and collectively referred to as the active layers.

In one embodiment, the different layers have the following range of thicknesses: anode 110, 500-5000 Å, in one embodiment 1000-2000 Å; hole injection layer 120, 50-2000 Å, in one embodiment 200-1000 Å; hole transport layer 130, 50-2000 Å, in one embodiment 200-1000 Å; electroactive layer 140, 10-2000 Å, in one embodiment 100-1000 Å; layer 150, 50-2000 Å, in one embodiment 100-1000 Å; cathode 160, 200-10000 Å, in one embodiment 300-5000 Å. The location of the electron-hole recombination zone in the device, and thus the emission spectrum of the device, can be affected by the relative thickness of each layer. The desired ratio of layer thicknesses will depend on the exact nature of the materials used.

Depending upon the application of the device 100, the electroactive layer 140 can be a light-emitting layer that is activated by an applied voltage (such as in a light-emitting diode or light-emitting electrochemical cell), or a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are described in Markus, John, *Electronics and Nucleonics Dictionary*, 470 and 476 (McGraw-Hill, Inc. 1966).

One or more of the new deuterated materials described herein may be present in one or more of the active layers of a device, in a particular embodiment the electron transport layer 150, also referred to as an electron transfer layer 150. The deuterated materials may be used in combination with non-deuterated materials, or in combination with other deuterated materials.

In some embodiments, the emissive material is also deuterated. In some embodiments, at least one additional layer includes a deuterated material. In some embodiments, the additional layer is the hole injection layer 120. In some embodiments, the additional layer is the hole transport layer 130.

In some embodiments, an electronic device has deuterated materials in any combination of layers selected from the group consisting of the hole injection layer, the hole transport layer, the electroactive layer, the electron injection layer and the electron transport layer.

In some embodiments, the devices have additional layers to aid in processing or to improve functionality. Any or all of these layers can include deuterated materials. In some embodiments, all the organic device layers comprise deuterated materials. In some embodiments, all the organic device layers consist essentially of deuterated materials.

a. Electroactive Layer

Host materials in combination with electroactive dopant materials can be used in layer 140. The host compounds can be used alone, or in combination with a second host material. Deuterated host compounds can be used as a host for dopants with any color of emission. In some embodiments, the deuterated compounds are used as hosts for green- or blue-emissive materials.

In some embodiments, the electroactive layer consists essentially of host and dopant combinations. Examples of host materials include, but are not limited to, chrysenes, phenanthrenes, triphenylenes, phenanthrolines, naphthalenes, anthracenes, quinolines, isoquinolines, quinoxalines, phenylpyridines, benzodifurans, and metal quinolinate complexes.

The amount of dopant material present in the electroactive composition is generally in the range of 3-20% by weight, based on the total weight of the composition; in some embodiments, 5-15% by weight. When a second host is present, the ratio of a first host to a second host is generally in the range of 1:20 to 20:1; in some embodiments, 5:15 to 15:5. In some embodiments, the first host material is at least 50% by weight of the total host material; in some embodiments, at least 70% by weight.

The dopant is an electroactive material which is capable of electroluminescence having an emission maximum between 380 and 750 nm. In some embodiments, the dopant emits red, green, or blue light.

Electroluminescent ("EL") materials which can be used as a dopant in the electroactive layer, include, but are not limited to, small molecule organic luminescent compounds, luminescent metal complexes, conjugated polymers, and mixtures thereof. Examples of small molecule luminescent compounds include, but are not limited to, chrysenes, pyrenes, perylenes, rubrenes, coumarins, anthracenes, thiadiazoles, derivatives thereof, and mixtures thereof. Examples of metal complexes include, but are not limited to, metal chelated oxinoid compounds. Examples of conjugated polymers include, but are not limited to poly(phenylenevinylenes), polyfluorenes, poly(spirobifluorenes), polythiophenes, poly(p-phenylenes), copolymers thereof, and mixtures thereof.

Examples of red light-emitting materials include, but are not limited to, periflanthenes, fluoranthenes, and perylenes. Red light-emitting materials have been disclosed in, for example, U.S. Pat. No. 6,875,524, and published US application 2005-0158577.

Examples of green light-emitting materials include, but are not limited to, diaminoanthracenes, and polyphenylenevinylene polymers. Green light-emitting materials have been disclosed in, for example, published PCT application WO 2007/021117.

Examples of blue light-emitting materials include, but are not limited to, diarylanthracenes, diaminochrysenes, diaminopyrenes, and polyfluorene polymers. Blue light-emitting materials have been disclosed in, for example, U.S. Pat. No. 6,875,524, and published US applications 2007-0292713 and 2007-0063638.

In some embodiments, the dopant is an organic compound. In some embodiments, the dopant is selected from the group consisting of a non-polymeric spirobifluorene compound and a fluoranthene compound.

In some embodiments, the dopant is a compound having aryl amine groups. In some embodiments, the electroactive dopant is selected from the formulae below:

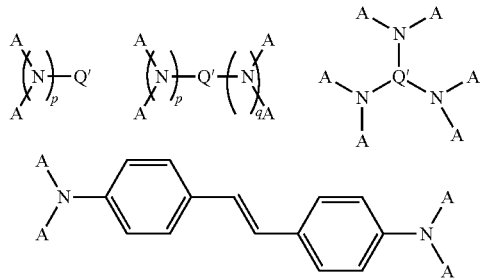

where:

A is the same or different at each occurrence and is an aromatic group having from 3-60 carbon atoms;

Q' is a single bond or an aromatic group having from 3-60 carbon atoms;

p and q are independently an integer from 1-6.

In some embodiments of the above formula, at least one of A and Q' in each formula has at least three condensed rings. In some embodiments, p and q are equal to 1.

In some embodiments, Q' is a styryl or styrylphenyl group.

In some embodiments, Q' is an aromatic group having at least two condensed rings. In some embodiments, Q' is selected from the group consisting of naphthalene, anthracene, chrysene, pyrene, tetracene, xanthene, perylene, coumarin, rhodamine, quinacridone, and rubrene.

In some embodiments, A is selected from the group consisting of phenyl, biphenyl, tolyl, naphthyl, naphthylphenyl, and anthracenyl groups.

In some embodiments, the dopant has the formula below:

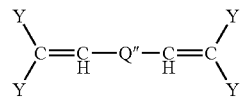

where:

Y is the same or different at each occurrence and is an aromatic group having 3-60 carbon atoms;

Q" is an aromatic group, a divalent triphenylamine residue group, or a single bond.

In some embodiments, the dopant is an aryl acene. In some embodiments, the dopant is a non-symmetrical aryl acene.

Some non-limiting examples of green dopants are compounds D1 through D8 shown below.

D1:
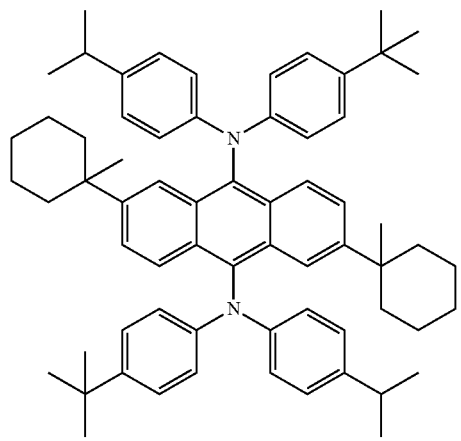
D2:
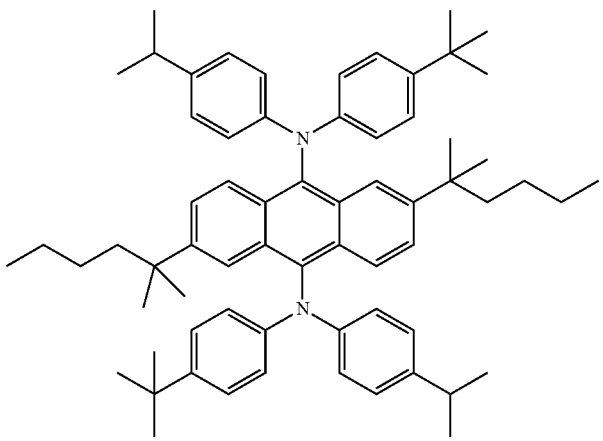
D3:
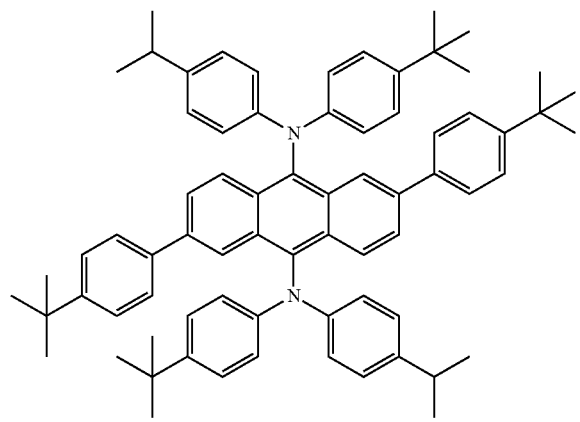
D4:
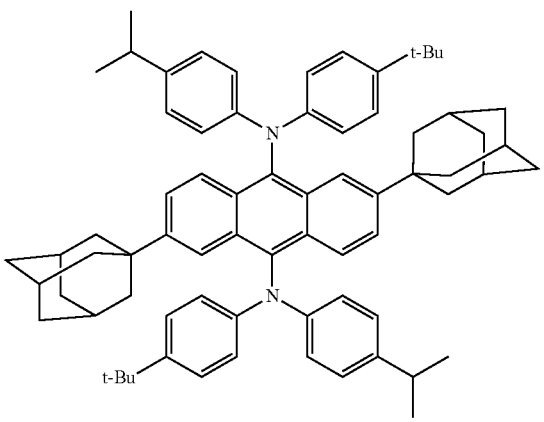
D5:
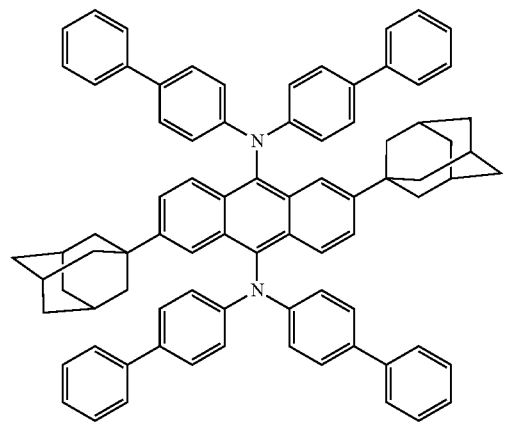
D6:
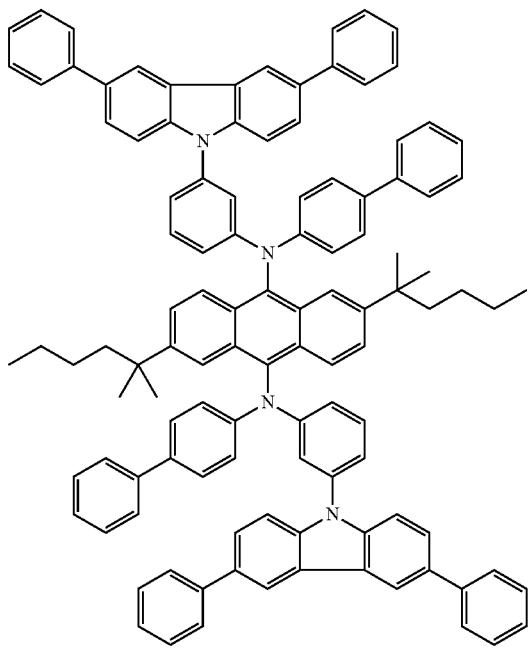

D7:
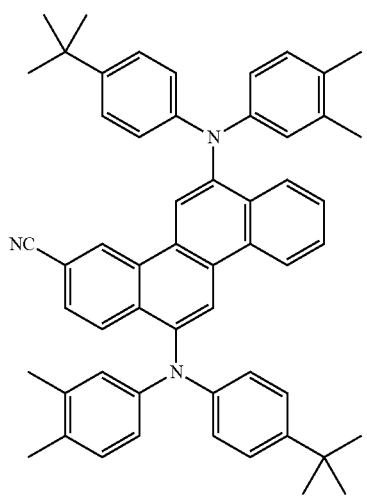
D8:
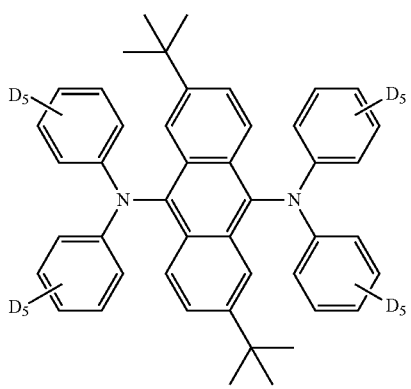
Some non-limiting examples of blue dopants are compounds D9 through D16 shown below.
D9:
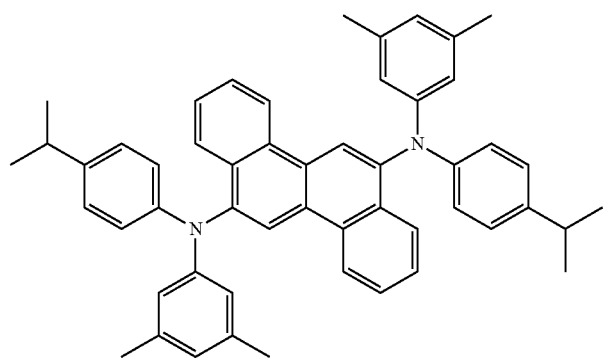
D10:
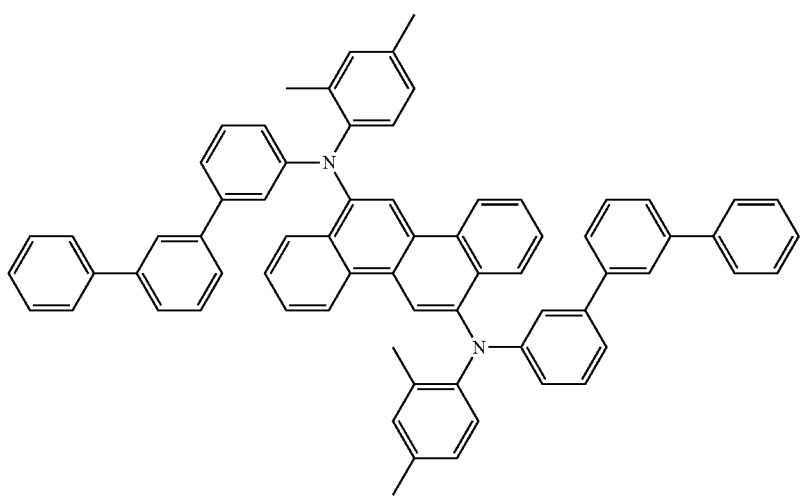

-continued
D11:
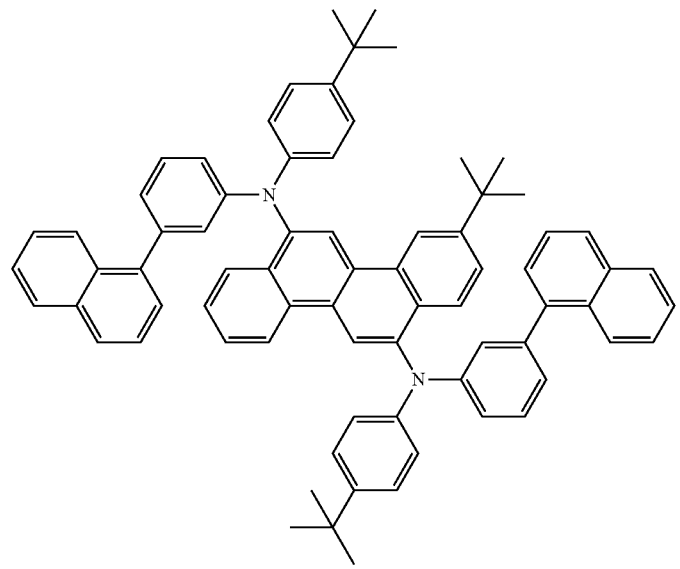
D12:
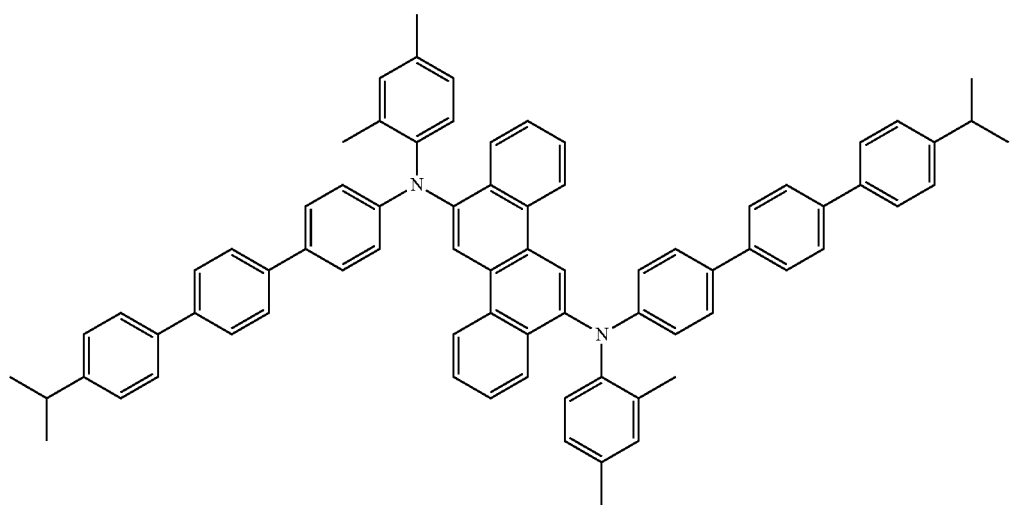

D13:
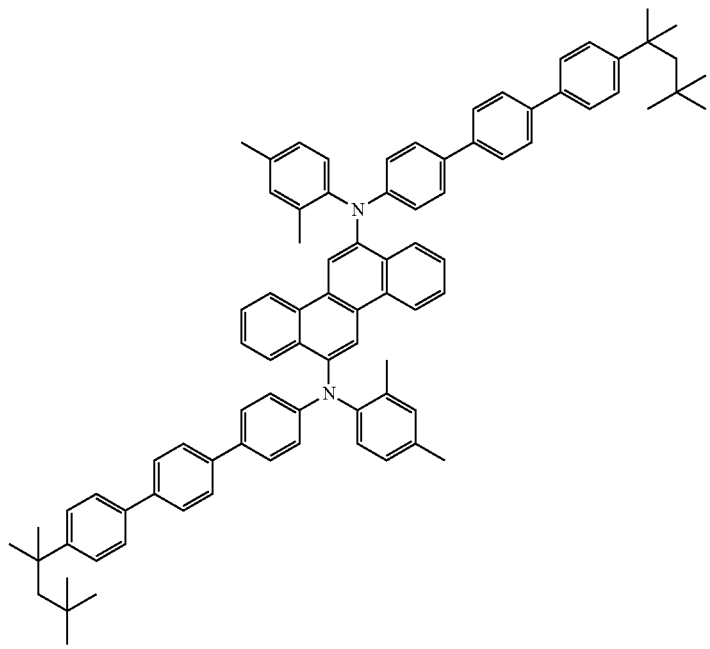
D14:
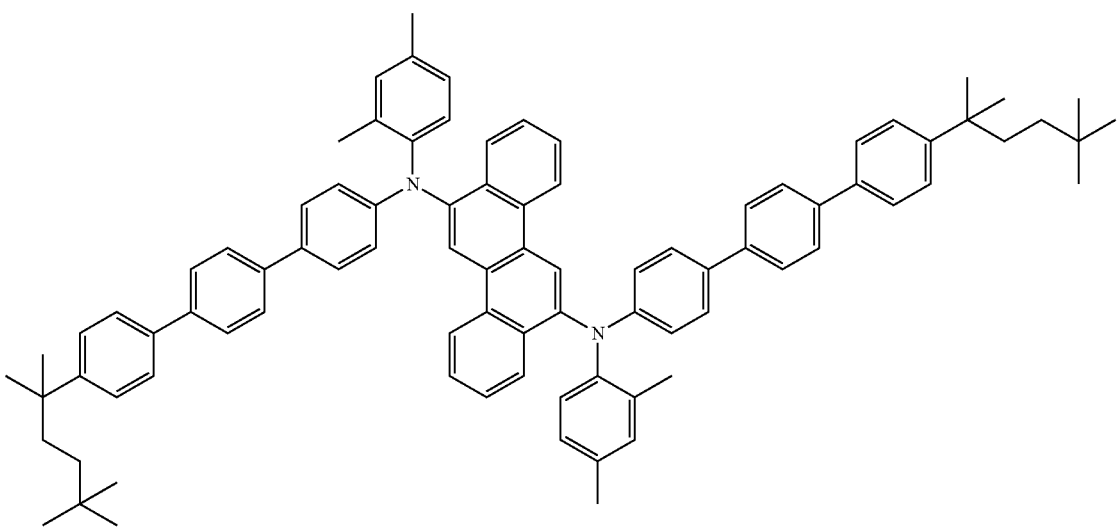

D15:

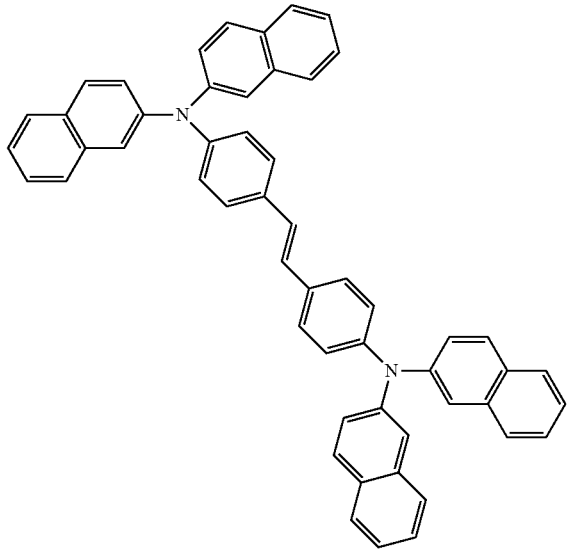

D16:

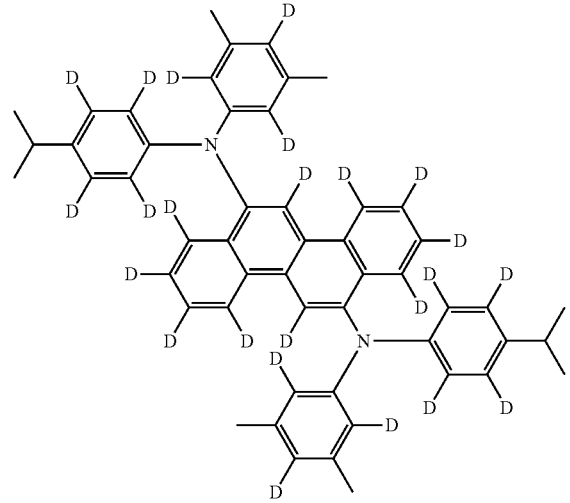

In some embodiments, the electroactive dopant is selected from the group consisting of amino-substituted chrysenes and amino-substituted anthracenes.

b. Other Device Layers

The other layers in the device can be made of any materials that are known to be useful in such layers.

The anode 110, is an electrode that is particularly efficient for injecting positive charge carriers. It can be made of, for example, materials containing a metal, mixed metal, alloy, metal oxide or mixed-metal oxide, or it can be a conducting polymer, or mixtures thereof. Suitable metals include the Group 11 metals, the metals in Groups 4-6, and the Group 8-10 transition metals. If the anode is to be light-transmitting, mixed-metal oxides of Groups 12, 13 and 14 metals, such as indium-tin-oxide, are generally used. The anode 110 can also comprise an organic material such as polyaniline as described in "Flexible light-emitting diodes made from soluble conducting polymer," Nature vol. 357, pp 477-479 (11 Jun. 1992). At least one of the anode and cathode is desirably at least partially transparent to allow the generated light to be observed.

The hole injection layer 120 comprises hole injection material and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. Hole injection materials may be polymers, oligomers, or small molecules. They may be vapour deposited or deposited from liquids which may be in the form of solutions, dispersions, suspensions, emulsions, colloidal mixtures, or other compositions.

The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like.

The hole injection layer can comprise charge transfer compounds, and the like, such as copper phthalocyanine and the tetrathiafulvalene-tetracyanoquinodimethane system (TTF-TCNQ).

In some embodiments, the hole injection layer comprises at least one electrically conductive polymer and at least one fluorinated acid polymer. Such materials have been described in, for example, published U.S. patent applications 2004-0102577, 2004-0127637, and 2005/205860

Examples of hole transport materials for layer 130 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1, 1'-biphenyl]-4,4'-diamine (TPD), 1,1-bis[(di-4-tolylamino) phenyl]cyclohexane (TAPC), N,N'-bis(4-methylphenyl)-N, N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino) benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino) styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-bis(naphthalen-1-yl)-N,N'-bis-(phenyl)benzidine (—NPB), and porphyrinic compounds, such as copper phthalocyanine. Commonly used hole transporting polymers are polyvinylcarbazole, (phenylmethyl)-polysilane, and polyaniline. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable. Examples of crosslinkable hole transport polymers can be found in, for example, published US patent application 2005-0184287 and published PCT application WO 2005/052027. In some embodiments, the hole transport layer is doped with a p-dopant, such as tetrafluorotetracyanoquinodimethane and perylene-3,4,9,10-tetracarboxylic-3,4, 9,10-dianhydride.

In some embodiments, the electron transport layer 150 comprises new deuterated compounds of the present claims. Examples of other electron transport materials which can be used in layer 150 include metal chelated oxinoid compounds, such as tris(8-hydroxyquinolato)aluminum (Alq$_3$); bis(2-methyl-8-quinolinolato)(para-phenyl-phenolato)aluminum(III) (BAlQ); and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ), and 1,3,5-tri(phenyl-2-benzimidazole)benzene (TPBI); quinoxaline derivatives such as 2,3-bis(4-fluorophenyl)quinoxaline; phenanthroline derivatives such as 9,10-diphenylphenanthroline (DPA) and 2,9-dimethyl-4,7-diphenyl-1,10-phenanthroline (DDPA); and mixtures thereof. The electron-transport layer may also be doped with n-dopants, such as Cs or other alkali metals. Layer 150 can function both to facilitate electron transport, and also serve as a buffer layer or confinement layer to prevent quenching of the exciton at layer interfaces. Preferably, this layer promotes electron mobility and reduces exciton quenching.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li- or Cs-containing organometallic compounds, LiF, CsF, and Li$_2$O can also be deposited between the organic layer and the cathode layer to lower the operating voltage.

It is known to have other layers in organic electronic devices. For example, there can be a layer (not shown) between the anode 110 and hole injection layer 120 to control the amount of positive charge injected and/or to provide bandgap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

The device can be prepared by a variety of techniques, including sequential vapor deposition of the individual layers on a suitable substrate. Substrates such as glass, plastics, and metals can be used. Conventional vapor deposition techniques can be used, such as thermal evaporation, chemical vapor deposition, and the like. Alternatively, the organic layers can be applied from solutions or dispersions in suitable solvents, using conventional coating or printing techniques, including but not limited to spin-coating, dip-coating, roll-to-roll techniques, slot die coating, ink-jet printing, screen-printing, gravure printing and the like.

The present invention also relates to an electronic device comprising at least one active layer positioned between two electrical contact layers, wherein the at least one active layer of the device includes deuterated compounds. Devices frequently have additional hole transport and electron transport layers.

To achieve a high efficiency LED, the HOMO (highest occupied molecular orbital) of the hole transport material desirably aligns with the work function of the anode, and the LUMO (lowest un-occupied molecular orbital) of the electron transport material desirably aligns with the work function of the cathode. Chemical compatibility and sublimation temperature of the materials are also important considerations in selecting the electron and hole transport materials.

It is understood that the efficiency of devices can be improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

The compounds of the invention often are photoluminescent and can be useful in applications other than OLEDs, such as oxygen sensitive indicators and as luminescent indicators in bioassays.

EXAMPLES

The following examples illustrate certain features and advantages of the present invention. They are intended to be illustrative of the invention, but not limiting. All percentages are by weight, unless otherwise indicated.

Synthesis of Ligand D$_6$-8-hydroxyquinoline

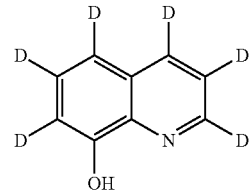 [SMILES: [2H]c1nc2c(O)c([2H])c([2H])c([2H])c2c([2H])c1[2H]]

A mixture of 8-hydroxyquinoline 93.00 g, 20.667 mmol), D$_2$O (60 mL) and 10% Pd/C (0.200 g) was placed in a Parr reactor under an atmosphere of nitrogen and heated to 180 C for 16 hours. The resulting mixture was added to diethyl ether (200 mL), the layers were separated and the organic layer was filtered through Celite. After evaporation of volatiles the resulting solid was purified using chromatography (20% DCM/hexane) to obtain 2.4 g (77% yield) of D$_6$-8-hydroxyquinoline product.

Synthesis of Deuterated Zirconium Compound

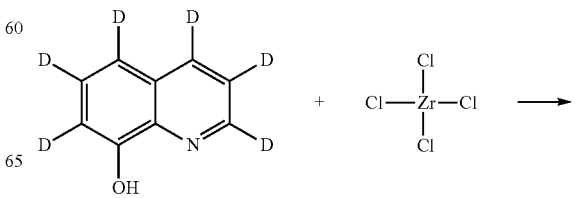

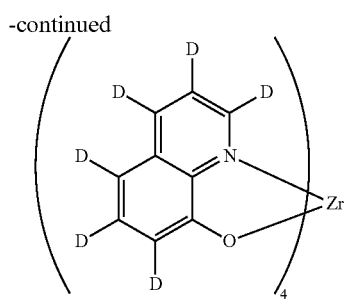

A 1.0 g quantity of zirconium chloride is placed in a glove box and mixed with 10 mL of dry methanol. Add to this mixture of zirconium chloride and methanol a stirred solution of 3.2 g of 8-hydroxyquinoline-D6 in 10 mL of dry methanol. Stirring produces a dense yellow precipitate upon combination of the zirconium and hydroxyquinoline reagents, continue strirring for 30 minutes under nitrogen and heat for reflux. Add 4.8 g tri-n-butylamine and reflux for 15 minutes, followed by filtering the deep yellow precipitate outside the glovebox. A three step washing procedure involves a methanol wash, followed by 1N ammonia wash and subsequent final methanol wash. Suction dry the extract using methylene chloride to produce a pale yellow solution with a yellow green photo-luminescent material, followed by precipitation with methanol.

Hydroxyquinoline starting materials can contain any of the following constituents: H, D, alkyl, alkoxy, aryl, aryloxy, siloxane, and silyl to produce final compound.

35 g (300 mM) 2-methyl-2-hexanol and 17.8 g anthracene (100 mM) were added to 50 mL trifluoroacetic acid and refluxed under nitrogen for overnight. Solution quickly darkened to a brown heterogeneous material. This was cooled to room temp., evaporated under a nitrogen stream and extracted into methylene chloride. Separated and dried organic layer over magnesium sulfate and evaporated to dryness. Extracted the resulting solid through a silica column with hexanes and recovered pale yellow solution. Evaporated to a thick yellow oil and recrystallized from acetone/methanol by slow cooling and recrystallization from methanol. NMR analysis confirmed the structure.

Synthesis of Intermediate (b)

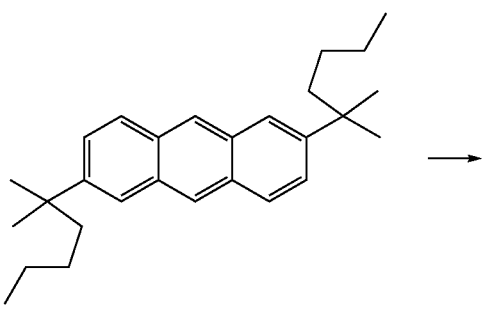

(a)

Synthesis of Dopant Materials (1) Dopant D6 was Prepared as Follows

Synthesis of Intermediate (a)

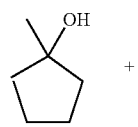 + 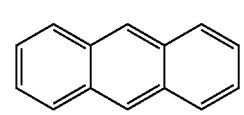 →

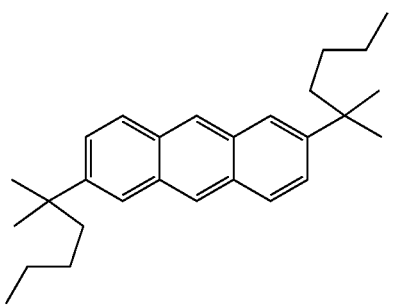

(a)

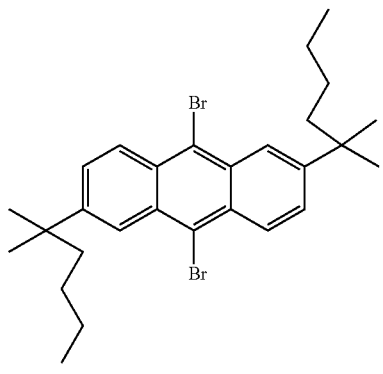

(b)

6.0 g (16 mM) intermediate (a) (pure 2,6 isomer) was taken into 100 mL dichloroethane and 2.10 mL bromine (40 mM) was added dropwise with stirring at room temperature for 4 hrs. This was poured into water and sodium sulfite was added to consume remaining bromine. This was then extracted into methylene chloride and the organic layer dried over magnesium sulfate. The resulting material was passed through alumina column with methylene chloride eluent and then evaporated and methanol added to precipitate a pale yellow solid. Yield ~7.2 g Synthesis of Intermediate (c)

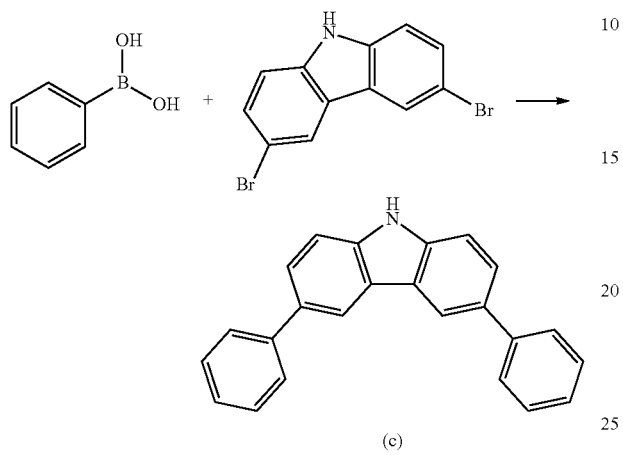

(c)

To 25 g of the bromo-carbazole (77.7 mM) in glove box was added 18.9 g (155 mM) boronic acid. To this was added 1.0 g Pd2 DBA3 (1.0 mM), 0.5 g P(t-Bu)3 (2.1 mM) and 20 g sodium carbonate (200 mM) and all was dissolved into 200 mL dioxane with 50 mL water. This was mixed and heated in a glove box in mantle at 50° C. for 1 hr then warmed gently (minimum rheostat setting) under nitrogen overnight. The solution immediately was dark purple and on reaching ~50 C it was dark brown. Added water to brown solution outside glove box and it separated an oily yellow layer. Added DCM and separated organic layer. Filtrate was dried over magnesium sulfate to give a light orange solution which generated white solid on evaporation. After evaporation to low volume and addition of hexanes, the white solid was filtered off. The solid was washed well with methanol until washings were colorless, and then rinsed with ether and suctioned dry to give 21 g white solid. The structure was confirmed by NMR analysis.

Synthesis of Intermediate (d)

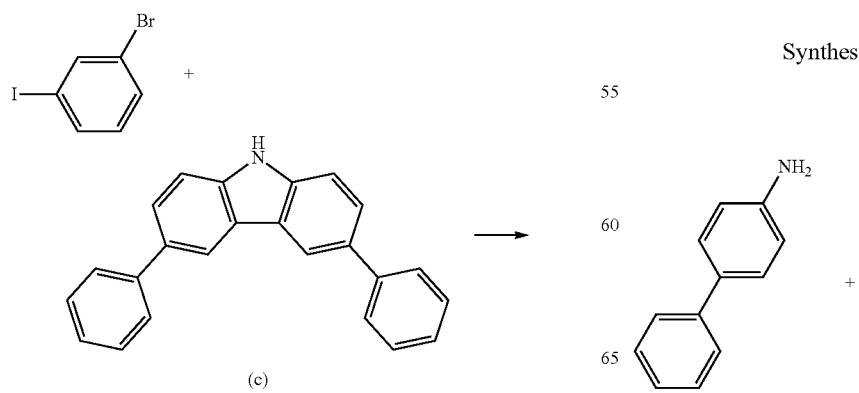

(c)

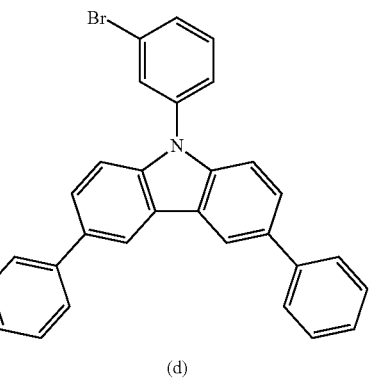

(d)

0.4 g Pd2 DBA3, 0.4 g 1,1'-bis(diphenylphosphine)ferrocene (DPPF) and 4.3 g sodium t-butoxide were mixed together and dissolved into 200 mL xylenes in glove box. Stirred 15 mins then added 25 g of 3-iodo-bromobenzene. Stirred 15 mins then added 10 g carbazole and the mix was brought to reflux. Refluxed o/n. using an air condenser. Solution immediately was dark purple/brown but on reaching ~80 C it was dark reddish brown and cloudy. After heating close to reflux overnight, the solution was dark brown and clear. Evaporated outside the glove box in nitrogen stream and then dissolved in DCM and extracted (soxhlet) through a bed of silica and basic alumina (stacked in soxhlet) using DCM/hexanes. Collected dark orange solution and evaporated to dryness. A dark orange oil remained. This was washed with methanol and then dissolve into ether and reprecipitated with methanol. The orange brown oil was evaporated to low volume in ether and then acetone/methanol was added to precipitate an off-white solid in yield of ~6.4 g. This was collected by filtration, washed with a little acetone and suctioned dry. The structure was confirmed by NMR analysis.

Synthesis of Intermediate (e)

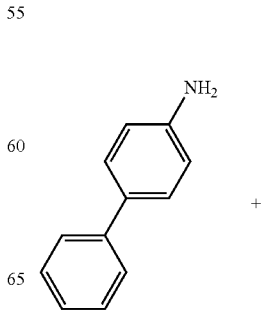

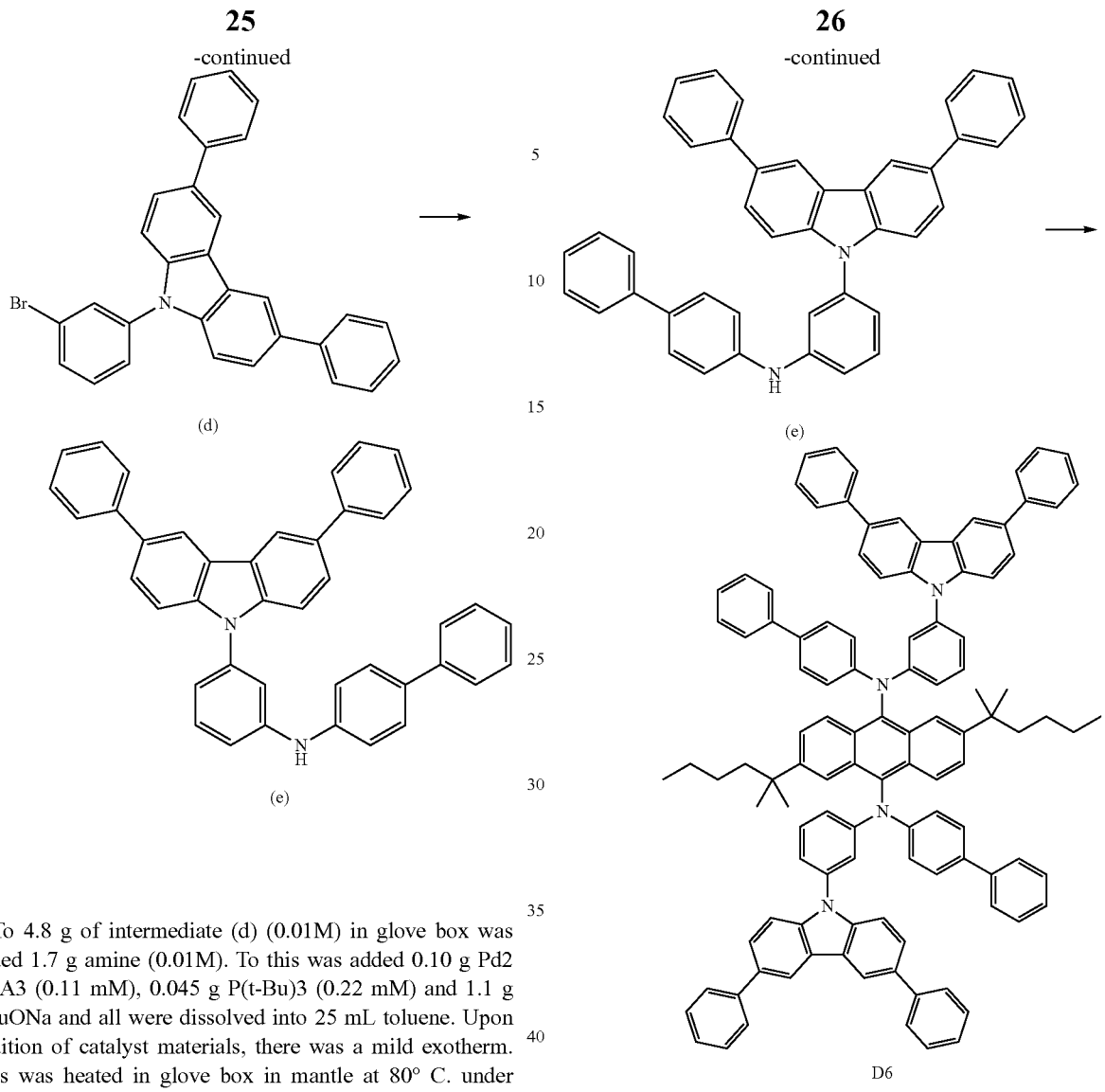

(d)

(e)

To 4.8 g of intermediate (d) (0.01M) in glove box was added 1.7 g amine (0.01M). To this was added 0.10 g Pd2 DBA3 (0.11 mM), 0.045 g P(t-Bu)3 (0.22 mM) and 1.1 g t-BuONa and all were dissolved into 25 mL toluene. Upon addition of catalyst materials, there was a mild exotherm. This was heated in glove box in mantle at 80° C. under nitrogen for 2 hr as a dark brown solution (thick). After cooling, the solution was worked up by β-alumina chromatography eluting with DCM. A dark yellow solution with bright purple/blue photoluminescence was collected. This was evaporated in nitrogen to low volume to form a viscous orange oil, which on cooling solidified to a dark yellow glass. This was stirred into methanol/DCM and allowed to crystallize as a pale yellow/white solid in ~5 g yield. The structure was confirmed by NMR analysis.

Synthesis of Dopant D6

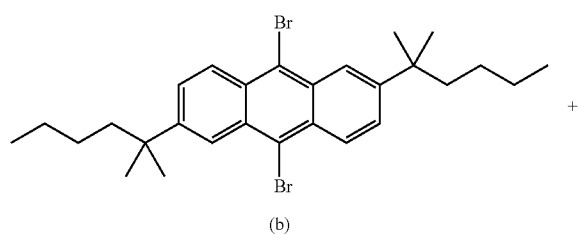

(b)

D6

To 1.32 g of intermediate (b) (2.5 mM) in glove box was added 2.81 g (5 mM) intermediate (e) and 0.5 g t-BuONa (5 mM) with 50 mL toluene. To this was added 0.2 g Pd2 DBA3 (0.2 mM), 0.08 g P(t-Bu)3 (0.4 mM) dissolved in 10 mL toluene. After mixing, the solution slowly exothermed and became yellow brown. This was mixed and heated in glove box in mantle at ~100° C. under nitrogen for 1 hr. Solution immediately was dark purple but on reaching ~80° C. it was dark yellow green with noticeable green luminescence. Stirred overnight at lowest rheostat setting. After cooling, the material was removed from glove box and filtered through an acidic-alumina plug eluting with toluene and methylene chloride. The dark orange solution was evaporated to low volume. This was passed through a silica column (using 60:40 toluene: hexanes). A yellow orange solution was collected which showed blue leading spots on TLC. This was redissolved in hexanes:toluene (80:20) and passed through acidic alumina eluting with 80% hexanes/toluene. The faster running blue bands (anthracene and monaminated anthracene) were discarded. The resulting yellow band was evaporated to low volume and crystallized from toluene/acetone/methanol. This was washed with methanol and hexanes and suctioned dry to obtain a free flowing microcrystalline yellow powder. The structure was confirmed by NMR analysis.

(2) Dopant D12,N6,N12-bis(2,4-dimethylphenyl)-N6,N12-bis(4"-isopropylterphenyl-4-yl)chrysene-6,12-diamine, was prepared as follows

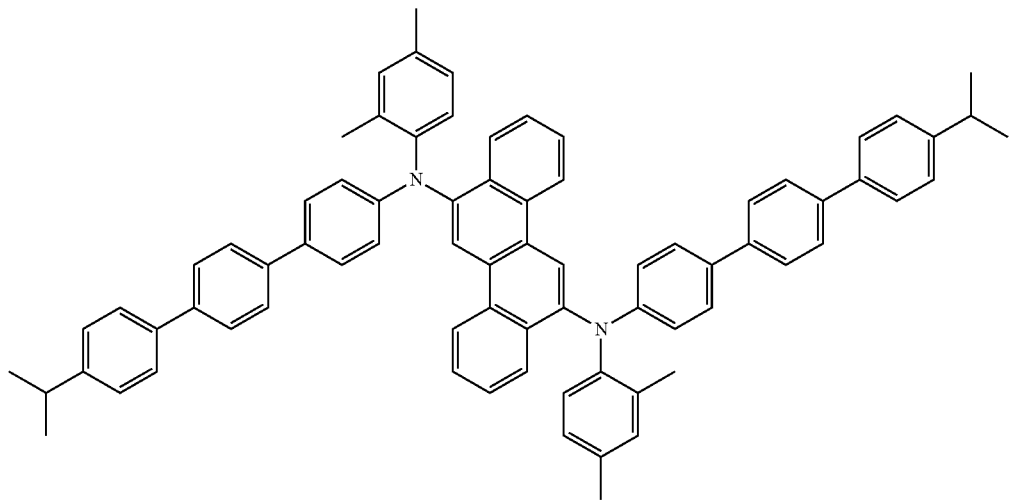 [SMILES: Cc1ccc(N(c2ccc(-c3ccc(-c4ccc(C(C)C)cc4)cc3)cc2)c2cc3c4ccccc4c(N(c4ccc(-c5ccc(-c6ccc(C(C)C)cc6)cc5)cc4)c4ccc(C)cc4C)cc3c3ccccc23)c(C)c1]

In a drybox, 6,12-dibromochrysene (0.54 g, 1.38 mmol), N-(2,4-dimethylphenyl)-N-(4'-isopropylterphenyl-4-yl)amine (1.11 g, 2.82 mmol), tris(tert-butyl)phosphine (0.028 g, 0.14 mmol) and tris(dibenzylideneacetone) dipalladium(0) (0.063 g, 0.069 mmol) were combined in round bottom flask and dissolved in 20 ml of dry toluene. The solution was stirred for a minute and followed by sodium tert-butoxide (0.29 g, 3.03 mmol) and 10 ml of dry toluene. A heating mantle was added and the reaction heated to 60 C for 3 days. The reaction mixture was then cooled to room temperature and filtered through a 1 inch plug of silica gel and one inch of celite, washing with toluene (500 mL). Removal of volatiles under reduced pressure gave a yellow solid. The crude product was purified further by silica gel column chromatography using a gradient of chloroform in hexanes (0% to 40%). Recrystallization from DCM and acetonitrile yielded 0.540 g (40%) of product as a yellow solid. $^1$H NMR (CDCl$_3$) is consistent with structure.

(3) Dopant D13,N6,N12-bis(2,4-dimethylphenyl)-N6,N12-bis(4"-tert-octylterphenyl-4-yl)chrysene-6,12-diamine, was made using a procedure analogous to the synthesis of D12

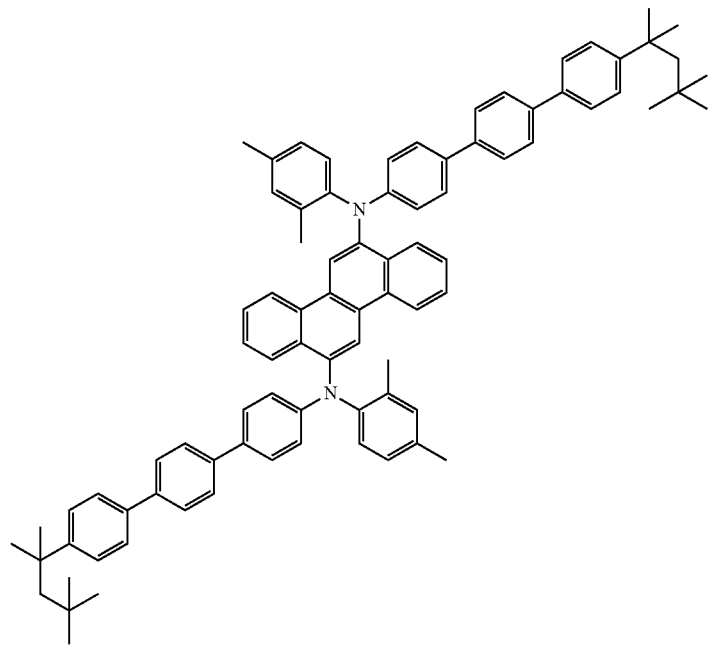 [SMILES: Cc1ccc(N(c2ccc(-c3ccc(-c4ccc(C(C)(C)CC(C)(C)C)cc4)cc3)cc2)c2cc3c4ccccc4c(N(c4ccc(-c5ccc(-c6ccc(C(C)(C)CC(C)(C)C)cc6)cc5)cc4)c4ccc(C)cc4C)cc3c3ccccc23)c(C)c1]

TABLE 1

Device Electron Transport Layers

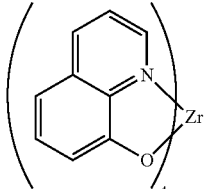

Comp. (A & B)

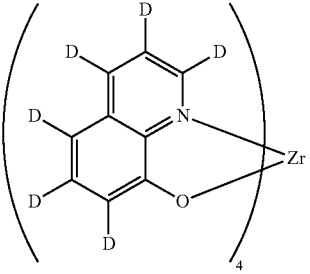

Deuterated ETL (C-F)

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 30 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Immediately before device fabrication the cleaned, patterned ITO substrates were treated with UV ozone for 10 minutes. Immediately after cooling, an aqueous dispersion of HIJ1 was spin-coated over the ITO surface and heated to remove solvent. After cooling, the substrates were then spin-coated with a solution of a hole transport material, and then heated to remove solvent. After cooling the substrates were spin-coated with the emissive layer solution, and heated to remove solvent. The substrates were masked and placed in a vacuum chamber. The electron transport layer was deposited by thermal evaporation, followed by a layer of CsF. Masks were then changed in vacuo and a layer of Al was deposited by thermal evaporation. The chamber was vented, and the devices were encapsulated using a glass lid, dessicant, and UV curable epoxy.

The OLED samples were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current needed to run the device. The unit is a cd/A. The power efficiency is the current efficiency multiplied by pi, divided by the operating voltage. The unit is lm/W. The device data is given in the following table.

TABLE 2

Device Performance

| Ex. | CIE (x, y) | Voltage (V) | E.Q.E. (%) | P.E. (lm/W) | Lifetest current density (mA/cm2) | Lifetest Luminance (nits) | Raw T50 (h) | Projected Lifetime T70 @1000 nits |
|---|---|---|---|---|---|---|---|---|
| Comp. (A) | 0.135, 0.131 | 4.6 | 5.4 | 4.0 | 129 | 6487 | 405 | 9726 |
| Comp. (B) | 0.135, 0.132 | 4.6 | 5.4 | 4.0 | 125 | 6293 | 444 | 10126 |
| Deuterated ETL (C) | 0.135, 0.135 | 4.6 | 5.5 | 4.1 | 133 | 6670 | 454 | 11431 |
| Deuterated ETL (D) | 0.135, 0.131 | 4.5 | 5.5 | 4.1 | 127 | 6368 | 464 | 10797 |
| Deuterated ETL (E) | 0.135, 0.130 | 4.5 | 5.5 | 4.0 | 125 | 6233 | 461 | 10344 |
| Deuterated ETL (F) | 0.135, 0.129 | 4.5 | 5.5 | 4.1 | 119 | 6077 | 507 | 10896 |

* All data @ 1000 nits, CE = current efficiency; CIEx and CIEy are the x and y color coordinates according to the C.I.E. chromaticity scale (Commission Internationale de L'Eclairage, 1931). RawT50 is the time in hours for a device to reach half of the initial luminance at the lifetest luminance given. Projected T70 is the projected lifetime at 1000 nits using an accelerator factor of 1.7.

It can be seen that with the deuterated compound of the invention, the lifetime of devices is increased, while maintaining other device properties.

Example 4

This example illustrates the preparation of some deuterated intermediate compounds that can be used in the electronic with controlled levels of deuteration.

Intermediate 4A

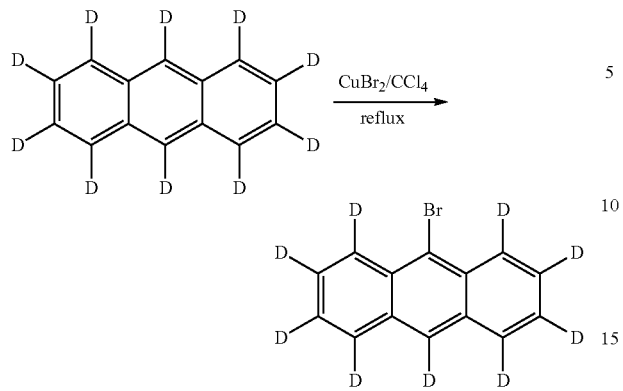

To a solution of anthracene-d10 (18.8 g, 0.10 mole) in CCl4 (500 mL) was added anhydrous cupric bromide (45 g, 0.202 mole) in one portion. The reaction mixture was stirred and heated under reflux for 12 hours. The brown cupric chloride is gradually converted to white cuprous bromide, and hydrogen bromide is gradually evolved (connected to base bath absorber). At the end of the reaction the cuprous bromide was removed by filtration, and the carbon tetrachloride solution was passed through a 35-mm. Chromatographic column filled with 200 g. of alumina. The column is eluted with 200 ml of CH2Cl2. The combined eluates are evaporated to dryness to give 24 g. (87%) of 9-bromoanthracene-d9 as a lemon-yellow solid. It contains impurity of the starting material (~2%) and the dibromo-byproduct (~2%). This material was used directly in further coupling reactions without purification. The intermediate can be further purified to by recrystallization using hexane or cyclohexane to give the pure compound.

Intermediate 4B

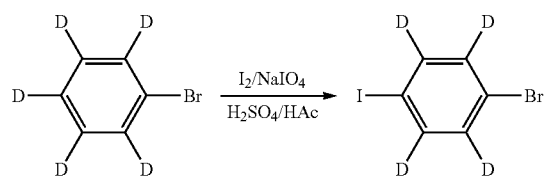 [SMILES: [2H]c1c([2H])c([2H])c(Br)c([2H])c1[2H] ; [2H]c1c([2H])c(I)c([2H])c([2H])c1Br]

To d5-bromobenzene (MW 162, 100 g, 0.617 mol), was added a mixture solvents of 93 mL of 50% $H_2SO_4$, and 494 mL of HOAc at rt. Then a pulverized $I_2$ (MW 254, 61.7 g, 0.243 mol) was added followed by pulverized $NaIO_4$ (MW 214, 26.4 g, 0.123 mol). The mixture was vigorously stirred and heated to 90° C. for 4 h. The dark purple color solution changed to a pale-orange-colored mixture containing a very fine white precipitate. The mixture was allowed to cool to rt overnight. During this time, the product precipitated as microcrystalline plates. The mixture was filtered and was washed twice 10% sodium thiosulfate $Na_2S_2O_3$ (50 mL) and then with water. It was dissolved in $CH_2Cl_2$ and run flash column. The light yellow, crystalline material was obtained 124 g (70%). The filtrate was extracted with $CH_2Cl_2$ (50 mL×3) and combined the $CH_2Cl_2$ washed twice 10% sodium thiosulfate $Na_2S_2O_3$ (50 mL) and then with water. After dried and evaporated the solvent and run flash column to give another 32 g of pure product (17.5%). Total is 156 g (yield 88%).

Intermediate 4C

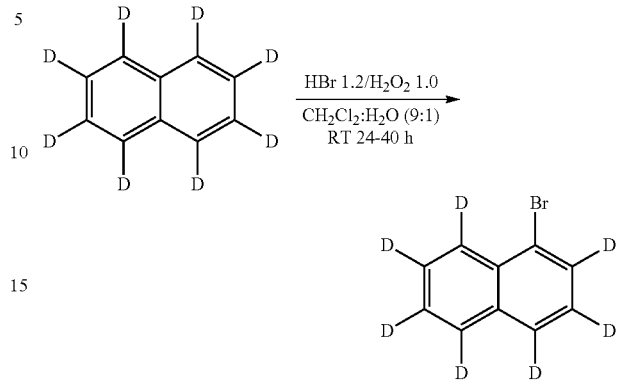

To a stirred solution of naphalene-d8 (MW 136, 68 g, 0.5 mole) in $CH_2Cl_2$ (800 mL): H20 (80 mL) and hydrobromic acid (MW: 81, d=1.49, 100 g; 67.5 mL of a 49% aq. solution; 0.6 mol) was slowly added hydrogen peroxide (FW: 34, d=1.1 g/mL, 56 g; 51.5 mL of a 30% aq. solution; 0.5 mol) over a period of 30 min at 10-15° C. The reaction was left at room temperature for 40 h whilst monitoring its progress by TLC. After the completion of bromination, the solvent was removed under reduced pressure and the crude product was washed twice 10% sodium thiosulfate Na2S2O3 (50 mL) and then with water. The pure product was isolated by flash column chromatography on silica gel (100-200 mesh) using hexane (100%) followed by distillation to give pure 1-bromo-naphthene-d7 as a clear liquid 85 g, the yield is around 80%.

Intermediate 4D

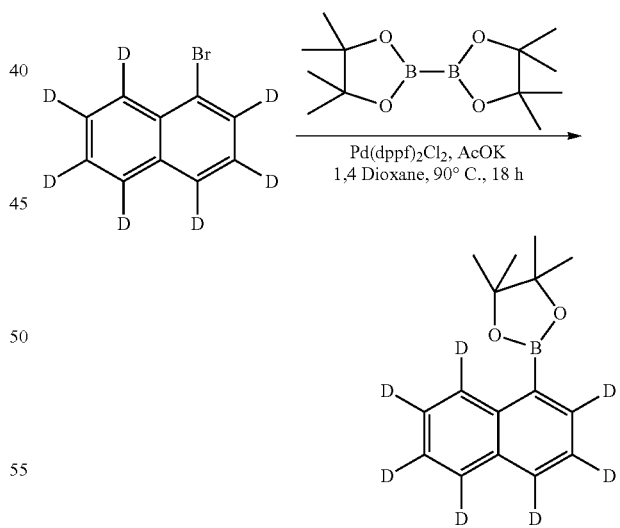

The mixture of 1-bromonaphthalene-d7 (21.4 g, 0.10 mol), bis(pinacolato)diboron (38 g, 0.15 mol), potassium acetate (19.6 g, 0.20 mol) in 300 ml of dry 1,4-dioxane was bubbled with nitrogen for 15 min. Then Pd(dppf)$_2$Cl$_2$—CH$_2$Cl$_2$(1.63 g, 0.002 mol) was added. The mixture was heated at 100° C. (oil bath) for 18 h. After cooling down the mixture was filtered through CELIT and then concentrated to 50 mL, then added water and extracted with ether for three times (100 mL×3). The organic layer was washed with water (3×) and brine (1×), dried over MgSO$_4$, filtered and concentrated. The residue was submitted to a silica gel column (eluent: hexane) to give a white liquid which has by products of naphalene, and diboronic ester. Thus further purification was conducted by distilliation to give a viscous clear liquid. Yield 21 g, 82%.

Intermediate 4E

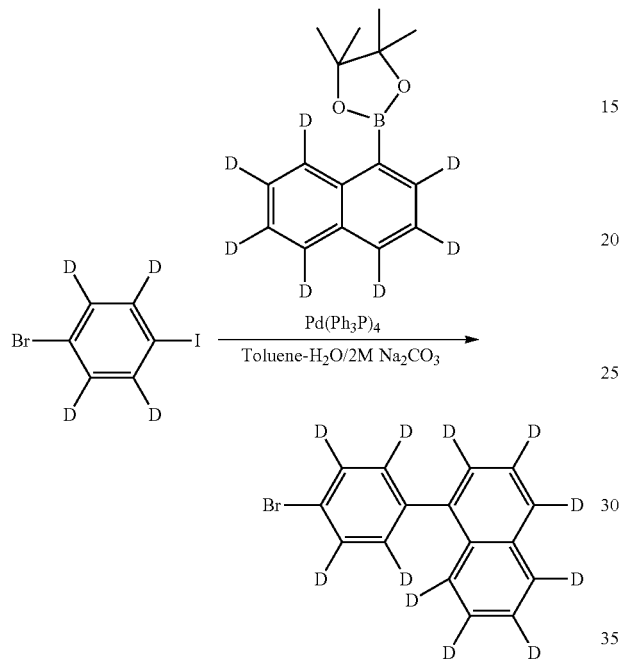

To a mixture of 1-bromo-4-iodo-benzene-D4 (10.95 g, 0.0382 mole) and 1-naphaleneboronic ester-D7 (10.0 g, 0.0383 mole) in Toluene (300 mL) was added Na$_2$CO$_3$ (12.6 g, 0.12 mole) and H2O (50 mL), aliquant (3 g). The mixture was bubbled with nitrogen for 15 min. Then Pd(PPh3)4 (0.90 g, 2%) was added. The mixture was refluxed for 12 h under a nitrogen atmosphere. After cooling down the reaction mixture was separated, the organic layer was washed with water and separated, dried and concentrated. Silica was added and concentrated. After evaporation the residue solvent, it was subject to run flash column using hexane as eluent to give crude product. Further purification was conducted by distillation (collect 135-140° C./100 mtorr) to give clear viscous liquid (8.76 g, yield 78%).

Intermediate 4F

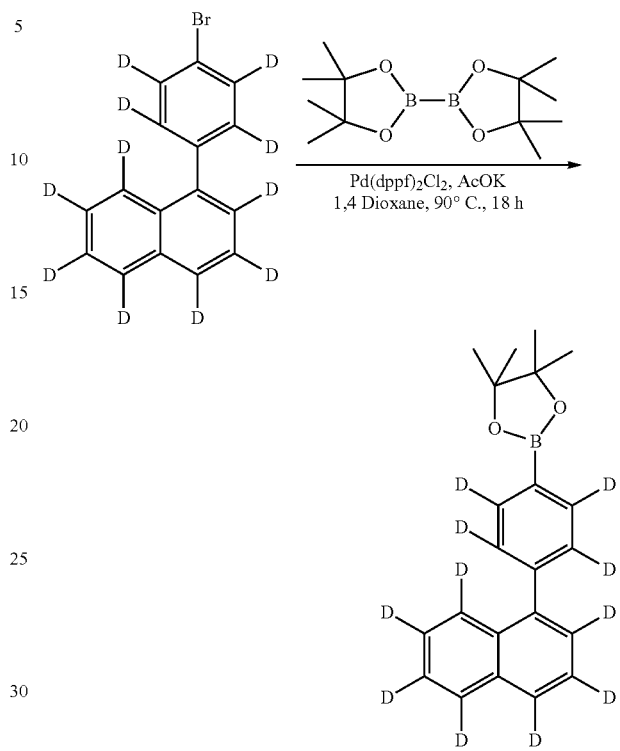

The mixture of 1-bromo-phenyl-4-naphthalene-d11 (22 g, 0.075 mole), bis(pinacolato)diboron (23 g, 0.090 mol), potassium acetate 22 g, 0.224 mol) in 200 ml of dry 1,4-dioxane was bubbled with nitrogen for 15 min. Then Pd(dppf)$_2$Cl$_2$.CH$_2$Cl$_2$ (1.20 g, 0.00147 mol) was added. The mixture was heated at 100° C. (oil bath) for 18 h. After cooling down the mixture was filtered through CELIT and then concentrated to 50 mL, then added water and extracted with ether for three times (100 mL×3). The organic layer was washed with water (3×) and brine (1×), dried over MgSO$_4$, filtered and concentrated. The residue was submitted to a silica gel column (eluent: hexane) to give a white liquid which has by products of naphalene, and diboronic ester. Thus further purification was conducted by run silica gel column again using hexane as eluent. After evaporate the solvent and concentrated to around 80 mL hexane and white crystal product was formed, it was filtrate to give 20.1 g of product, yield 81%.

Intermediate 4G

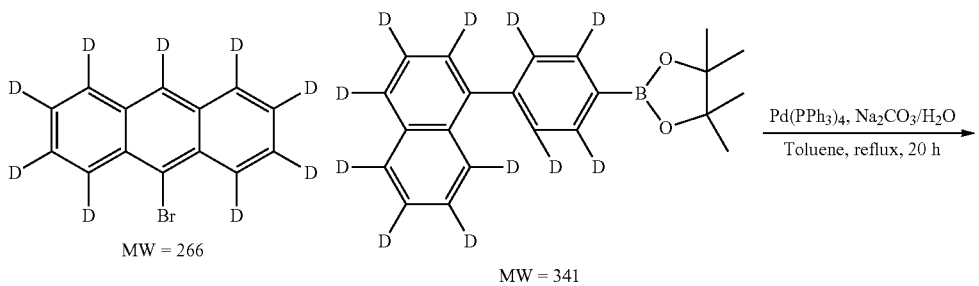

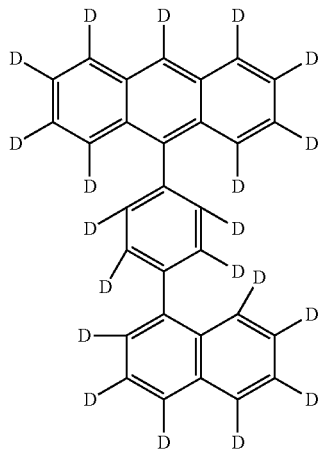

To the intermediate 4A (18.2 g) and intermediate 4F boronic ester (25.5 g) in Toluene (500 mL) was added Na$_2$CO$_3$ (31.8 g) and H2O (120 mL), aliquant (5 g). The mixture was bubbled with nitrogen for 15 min. Then Pd(PPh3)4 (1.5 g, 1.3%) was added. The mixture was refluxed for 12 h under a nitrogen atmosphere. After cooling down the reaction mixture was separated, the organic layer was washed with water and separated, dried and concentrated to ~50 mL and poured into MeOH. The solid was filtered to give a yellow crude product (~28.0 g). The crude product was washed with water, HCl (10%), water and methanol. It was redissolved in CHCl$_3$, dried over MgSO4, filtered. The filtrate was added silica gel, concentrated and dried, purified on silica gel (0.5 Kg) using hexane only as eluent (total of 50 L hexane passed—recycled using only 5 L of hexane) to give the white product.

Intermediate 4H

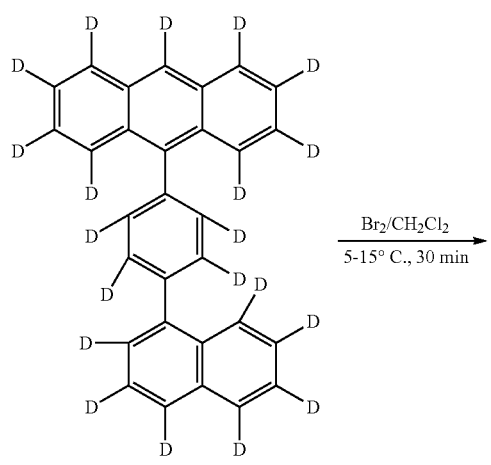

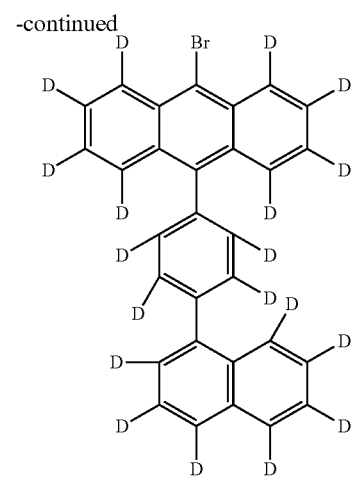

Into a ice-bath cooled solution of 9-(4-naphthalen-1-yl) phenylanthracene-D20, Intermediate 4G, (MW 400.6, 20.3 g, 0.05 mole) in CH2Cl2 (450 mL) was added slowly (20 min) of bromine (MW 160, 8.0 g, 0.05 mole) dissolved in CH2Cl2 (150 mL). The reaction immediately occurred and the color changed to light yellow. Add a solution of Na2S2O3 (2M 100 mL) and stirred for 15 min. Then separated the water layer and the organic phase was washed by Na2CO3 (10%, 50 mL), followed by three times of water. Separated and then dried by MgSO4 and after evaporated the solvent till 100 mL left. Powered into methanol (200 mL) and filtered to give 23.3 g of pure compound (MW 478.5, yield 0.97.5%) HPLC shows 100% purity.

Intermediate 4I

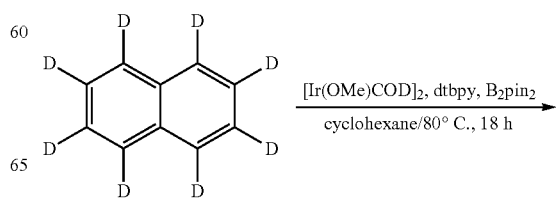

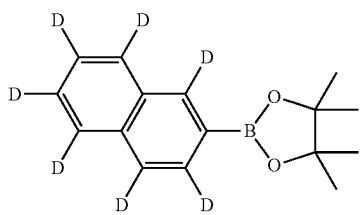

The mixture of naphthalene-D8 (13.6 g, 0.10 mole), bis(pinacolato)diboron (27.93 g, 0.11 mole), di-mu-methoxobis(1,5-cyclooctadiene)diiradium (I) [Ir(OMe)COD]$_2$ (1.35 g, 2 mmole, 2%) and 4,4'-di-tert-butyl-2,2'-bipyridine (1.1 g, 4 mmole) was added to cyclohexane (200 mL). The mixture was degassed with N2 for 15 min, then heated at 85° C. (oil bath) overnight (dark brown solution). The mixture was passed through a pad of silica gel. The fractions were collected and concentrated until dry. Hexane was added. The filtrate was concentrated (liquid) and passed through a silica gel column, rinsing with hexane to give clear liquid, it was not pure and was purified again by silica gel column, rinsing with hexane followed by distillation at 135° C./100 mmtorr to give pure white viscous liquid and it solidified to give a white powder (18.5 g. Yield 70%).

Intermediate 4J

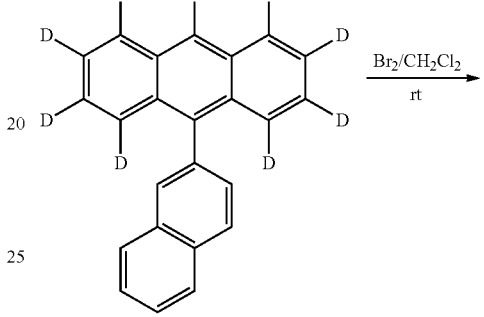

Into a RBF (100 mL) was added 9-bromoanthracene-d9 (MW 266, 2.66 g, 0.01 mole), naphthelen-2-boronic acid (MW 172, 1.72 g, 0.01 mol), followed by the addition of toluene (30 mL), The mixture was purged with N2 for 10 min. Then Na$_2$CO$_3$ (2M, 10 mL (2.12 g) 0.02 mole) dissolved in the water (10 mL) was added. The mixture was continued to purge with N$_2$ for 10 min. A catalyst amount of Pd(PPh$_3$)$_4$ (0.25 g, 2.5%, 0.025 mmol) was added. The mixture was refluxed overnight. Separated the organic layer then poured into metahol, washed with water, HCl (10%), water and methanol. It gives 2.6 g pure white product. (Yield: 83%).

Intermediate 4K

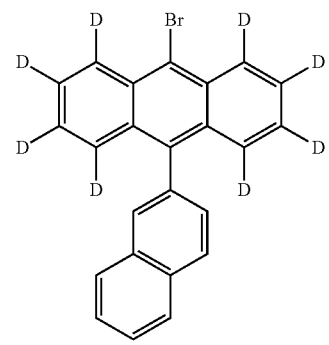

A solution of (2.6 g 0.0083 mole) 9-2'-naphthyl-anthacene-d9, intermediate 4J in CH2Cl2 (50 mL) was added dropwise a solution of bromine (133 g, 0.0083 mole) in CH2Cl2 (5 mL) and stirred for 30 min. Add a solution of Na2S2O3 (2M 10 mL) and stirred for 15 min. Then separated the water layer and the organic phase was washed by Na2CO3 (10%, 10 mL), followed by three times of water. Separated and then dried by MgSO4 and after evaporated the solvent till 20 mL left. Powered into methanol (100 mL) and filtered give pure compound (3.1 g, yield 96%).

Intermediate 4L

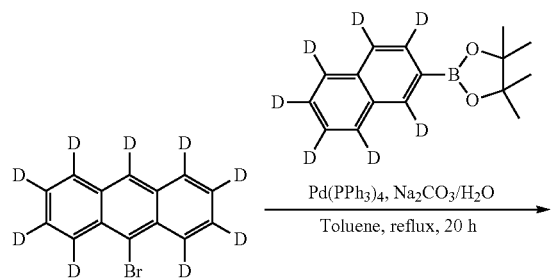

Intermediate 4M

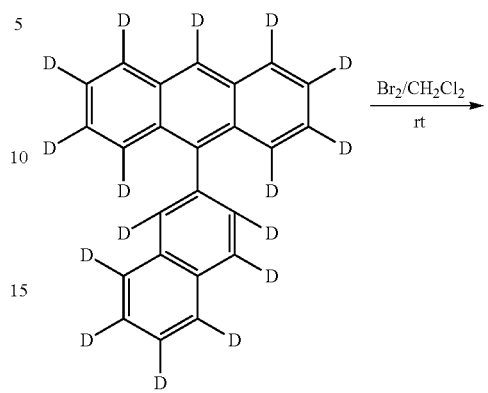

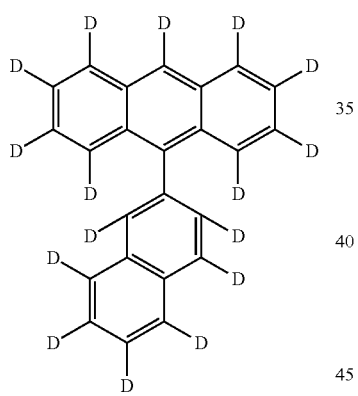

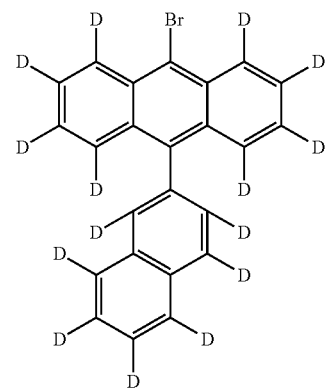

To a mixture of 9-bromoanthracene-D9, intermediate 4K (2.66 g, 0.01 mole) and 4,4,5,5-tetramethyl-2-(naphthalene-2-yl-D7)-1,3,2-dioxaborolane (2.7 g, 0.011 mole) in Toluene (~60 mL) was added $Na_2CO_3$ (4.0 g, 0.04 mole) and H2O (20 mL). The mixture was bubbled with nitrogen for 15 min. Then $Pd(PPh_3)_4$ (0.20 g, 2.0%) was added. The mixture was refluxed for 18 h under a nitrogen atmosphere (yellow solids). After cooling down the reaction mixture, it was poured into MeOH (200 mL). The solid was filtered to give a yellow crude product. The crude product was washed with water, and methanol. It was redissolved in $CHCl_3$, dried over MgSO4, filtered. The filtrate was added silica gel, concentrated and dried, purified on silica gel using hexane as eluent to give the pure product (3.0 g, yield 94%).

A solution of 9-2'-naphthyl-anthacene-d9, intermediate 4 L (2.8 g 0.00875 mole) in CH2Cl2 (50 mL) was added dropwise a solution of bromine (1.4 g, 0.00875 mole) in CH2Cl2 (5 mL) and stirred for 30 min. Then a solution of Na2S2O3 (2M 10 mL) was added and the mixture was stirred for 15 min. Then separated the water layer and the organic phase was washed by Na2CO3 (10%, 10 mL), followed by three times of water. Separated and then dried by MgSO4 and after evaporated the solvent till 20 mL left. Powered into methanol (100 mL) and filtered give pure compound (3.3 g, yield 95%).

Example 5

This example illustrates the synthesis of a host compound from Intermediate 4H and Intermediate 4I.

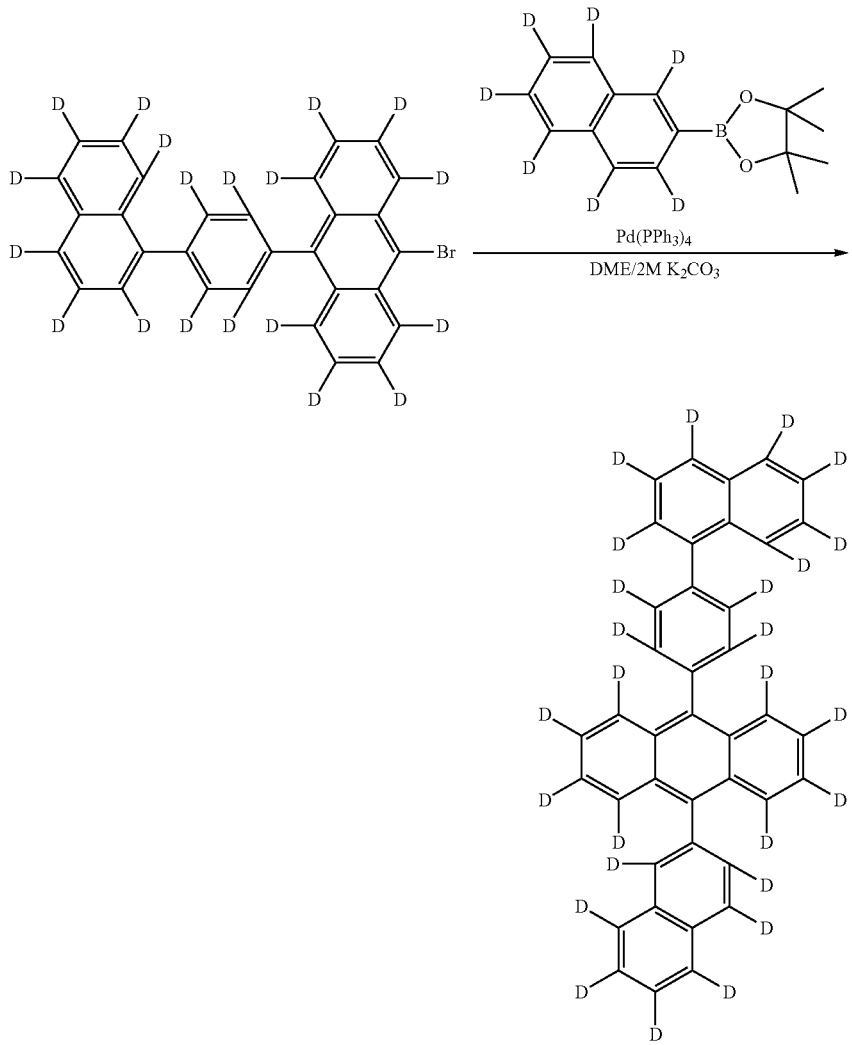

To a mixture of 9bromo-10-(4-naphthalen-1-yl)phenylanthracene-D19 intermediate 4H (14.84 g, 0.031 mole) and 2-naphthalen boronic ester intermediate 4I (10.0 g, 0.038 mole) in DME (350 mL) was added $K_2CO_3$ (12.8 g, 0.093 mole) and H2O (40 mL). The mixture was bubbled with nitrogen for 15 min. Then Pd(PPh3)4 (0.45 g, 1.3%) was added. The mixture was refluxed for 12 h under a nitrogen atmosphere. After cooling down the reaction mixture was concentrated to ~150 mL and poured into MeOH. The solid was filtered to give a light yellow crude product. The crude product was washed with water, and methanol. It was redissolved in $CHCl_3$, dried over MgSO4, filtered. The filtrate was added silica gel, concentrated and dried, purified on silica gel (0.5 Kg) using hexane:chloroform (3:1) as eluent to give the white product. (15 g, yield 91%)

Example 6

This example illustrates the synthesis of another host compound from Intermediate 4K.

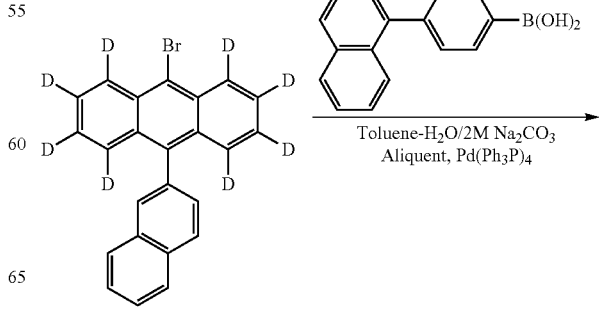

-continued

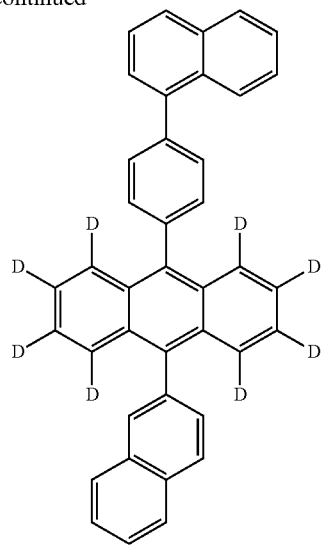

Into a RBF (100 mL) was added 9-bromo-10-(naphthalene-2-yl)anthracene, intermediate 4K (1.96 g, 0.05 mol), 4-(naphthalene-1-yl)phenylboronic acid (1.49 g, 0.06 mol), followed by the addition of toluene (30 mL). The mixture was purged with N2 for 10 min. Then $Na_2CO_3$ (1.90 g, 0.018 mole) dissolved in the water (8 mL) was added, followed by Aliquent (1 mL). The mixture was continued to purge with N2 for 10 min. A catalyst amount of Pd(PPh3)4 (116 mg) was added. The mixture was refluxed overnight. After split of aqueous phase, organic layer was poured into methanol (100 mL) to collect the white solid. It was filtrated and further purification was conducted by running the silica gel column using chloroform:hexane (1:3) to give pure white compound (2.30 g, yield 90%).

Example 7

This example illustrates the synthesis of another host compound from Intermediate 4K and Intermediate 4F.

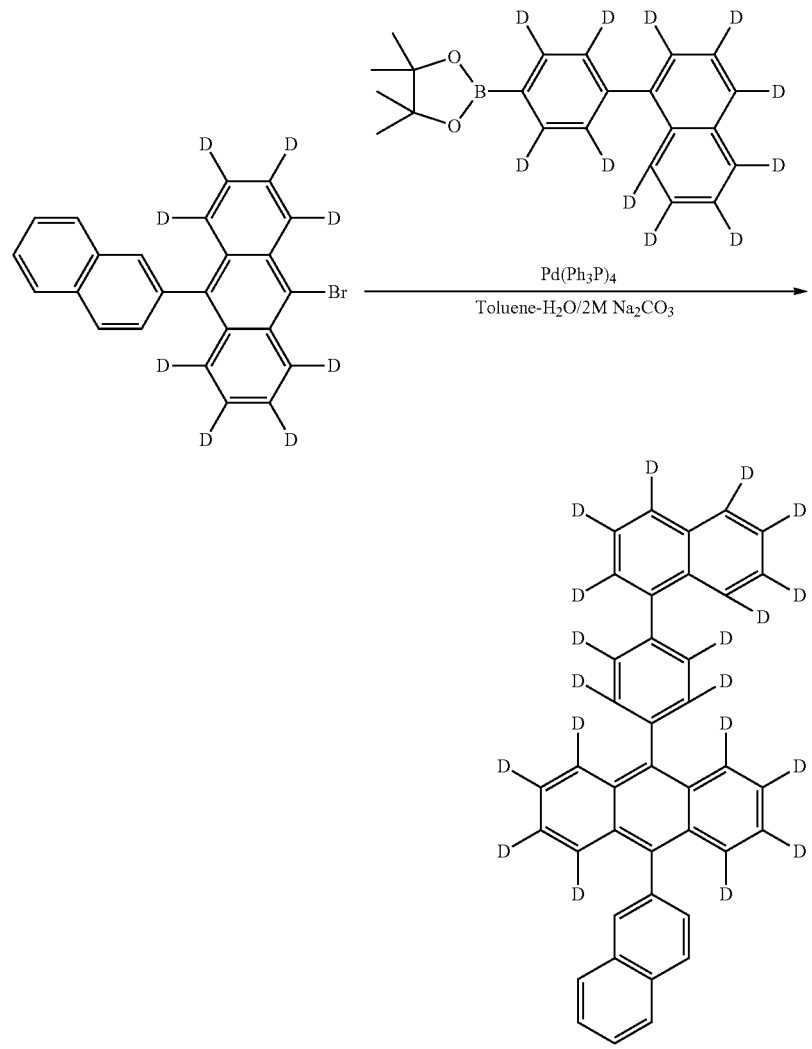

Into a RBF (100 mL) was added 9-bromo-10-(naphthalene-2-yl)anthracene-D8, intermediate 4K (0.70 g, 0.0018 mol), 4-(naphthalene-1-yl)phenylboronic acid-D11, intermediate 4F (0.7 g, 0.002 mol), followed by the addition of toluene (10 mL). The mixture was purged with N2 for 10 min. Then Na₂CO₃ (0.64 g, 0.006 mole) dissolved in the water (3 mL) was added, followed by Aliquent 0.1 mL). The mixture was continued to purge with N2 for 10 min. A catalyst amount of Pd(PPh3)4 (0.10 g) was added. The mixture was refluxed overnight. After split of aqueous phase, organic layer was poured into methanol (100 mL) to collect the white solid. It was filtrated and further purification was conducted by running the silica gel column using chloroform:hexane (1:3) to give pure white compound (0.90 g, is yield 95%).

Other host compounds can be prepared in an analogous manner.

It can be seen that with the combination having the deuterated compound of the invention, the lifetime of the device is increased, while maintaining other device properties.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A zirconium compound consisting of:

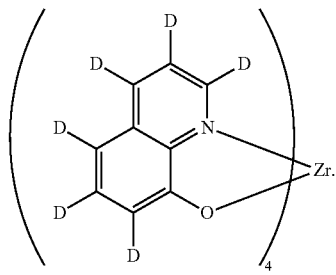

2. An organic electronic device comprising a first electrical contact layer, a second electrical contact layer, an electron transport layer and at least one electroactive layer between the first and second contact layers, wherein the electron transport layer is adjacent to the second electrical contact layer, and wherein the electron transport layer comprises a compound comprising:

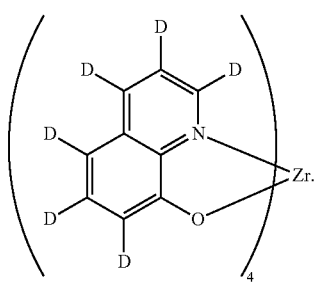

* * * * *